United States Patent
Hirokawa et al.

(10) Patent No.: US 12,256,994 B2
(45) Date of Patent: Mar. 25, 2025

(54) SYSTEMS AND METHODS FOR COMBINING FUNDUS IMAGES OF AN EYE

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

(*) Notice: Subject to any disclaimer, the term of this patent is extended or adjusted under 35 U.S.C. 154(b) by 286 days.

(21) Appl. No.: 17/615,046

(22) PCT Filed: May 31, 2019

(86) PCT No.: PCT/JP2019/021868
§ 371 (c)(1),
(2) Date: Nov. 29, 2021

(87) PCT Pub. No.: WO2020/240867
PCT Pub. Date: Dec. 3, 2020

(65) Prior Publication Data
US 2022/0230307 A1    Jul. 21, 2022

(51) Int. Cl.
*A61B 3/12* (2006.01)
*A61B 3/00* (2006.01)
*G06T 7/00* (2017.01)

(52) U.S. Cl.
CPC .............. *A61B 3/12* (2013.01); *A61B 3/0025* (2013.01); *A61B 3/0058* (2013.01);
(Continued)

(58) Field of Classification Search
CPC ....... A61B 3/12; A61B 3/0025; A61B 3/0058; G06T 7/0012; G06T 2207/10101;
(Continued)

(56) References Cited

U.S. PATENT DOCUMENTS

2009/0136100 A1   5/2009   Shinohara
2011/0279776 A1   11/2011  Spaide
(Continued)

FOREIGN PATENT DOCUMENTS

JP   H04-336677 A   11/1992
JP   2001-014444 A   1/2001
(Continued)

OTHER PUBLICATIONS

Ishikawa et al, "Preoperative estimation of distance between retinal break and limbus with wide-field fundus imaging: Potential clinical utility for conventional scleral buckling" (published at PLOS One, https://doi.org/10.1371/journal.pone.0212284, Feb. 2019).*
(Continued)

*Primary Examiner* — Casey L Kretzer
(74) *Attorney, Agent, or Firm* — Foley & Lardner LLP

(57) ABSTRACT

An image processing method includes acquiring a first direction fundus image imaged in a state in which an examined eye is directed in a first direction, and a second direction fundus image imaged in a state in which the examined eye is directed in a second direction different to the first direction, generating a combined image for analyzing a fundus-peripheral portion of the examined eye by combining the first direction fundus image and the second direction fundus image, and outputting the combined image.

9 Claims, 18 Drawing Sheets

(52) U.S. Cl.
CPC .. *G06T 7/0012* (2013.01); *G06T 2207/10101* (2013.01); *G06T 2207/20212* (2013.01); *G06T 2207/30041* (2013.01); *G06T 2207/30101* (2013.01)

(58) Field of Classification Search
CPC . G06T 2207/20212; G06T 2207/30041; G06T 2207/30101
See application file for complete search history.

(56) References Cited

U.S. PATENT DOCUMENTS

| | | | |
|---|---|---|---|
| 2012/0095349 A1* | 4/2012 | Peyman | A61B 3/10 606/4 |
| 2014/0039048 A1* | 2/2014 | Bavik | C07C 323/32 514/459 |
| 2019/0117064 A1* | 4/2019 | Fletcher | H04M 1/72409 |
| 2020/0214556 A1 | 7/2020 | Aoki et al. | |

FOREIGN PATENT DOCUMENTS

| | | | | |
|---|---|---|---|---|
| JP | 2019-004956 A | | 1/2019 | |
| WO | WO-2017180965 A1 | * | 10/2017 | ........... A61B 3/0025 |
| WO | WO-2018/069346 A1 | | 4/2018 | |

OTHER PUBLICATIONS

Office Action issued in corresponding Japanese Patent Application No. 2021-522602 dated Mar. 14, 2023 (9 pages).

Japanese Office Action dated Jul. 2, 2024 in Japanese Application No. 2023-097994 (7 pages).

Office Action issued in corresponding Japanese Patent Application No. 2023-097994, dated Feb. 4, 2025, with English translation (9 pages).

* cited by examiner

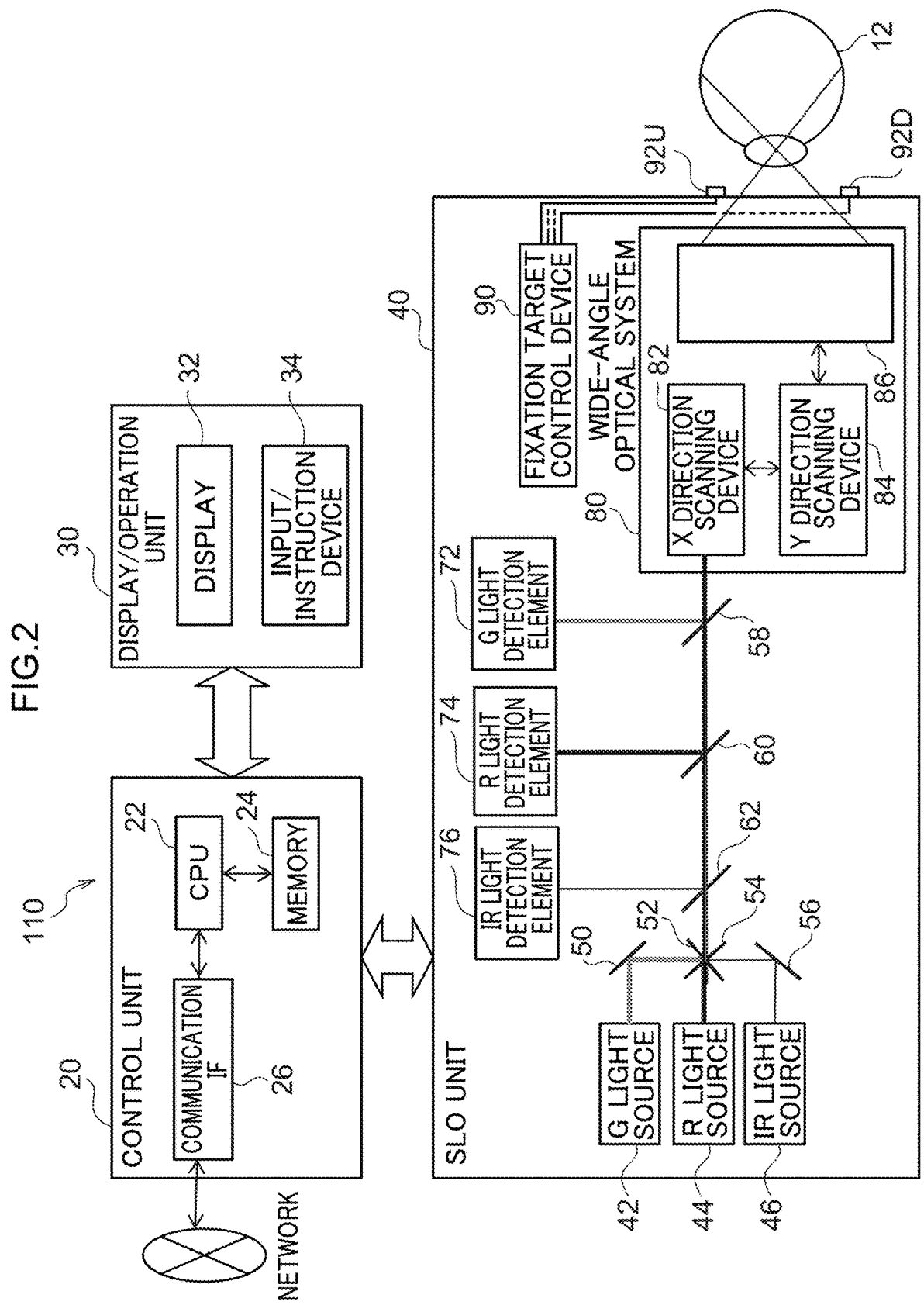

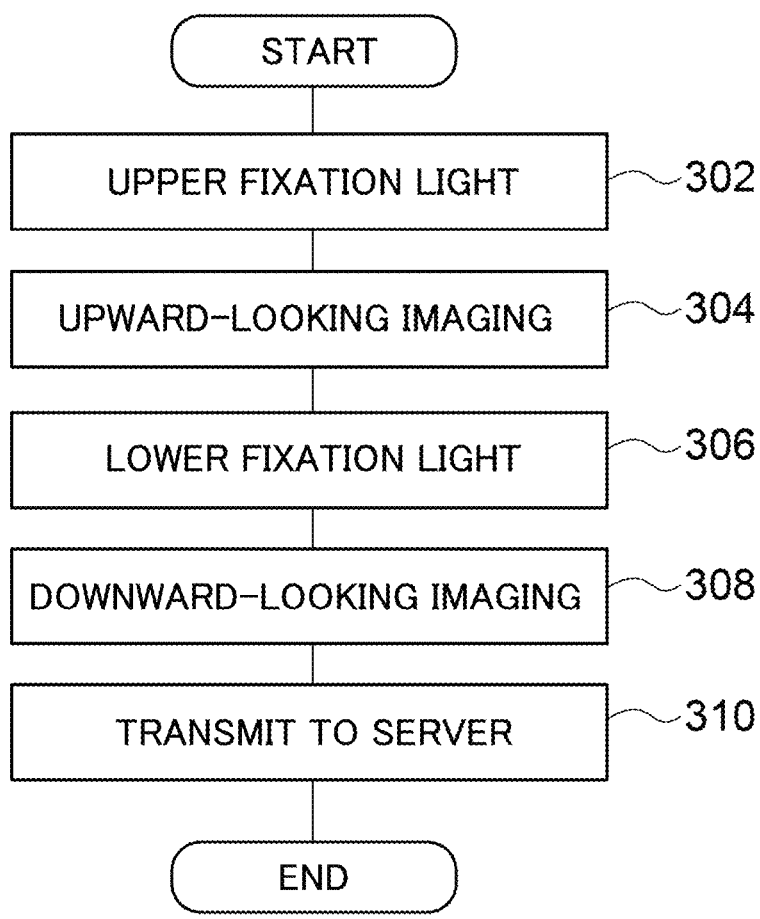

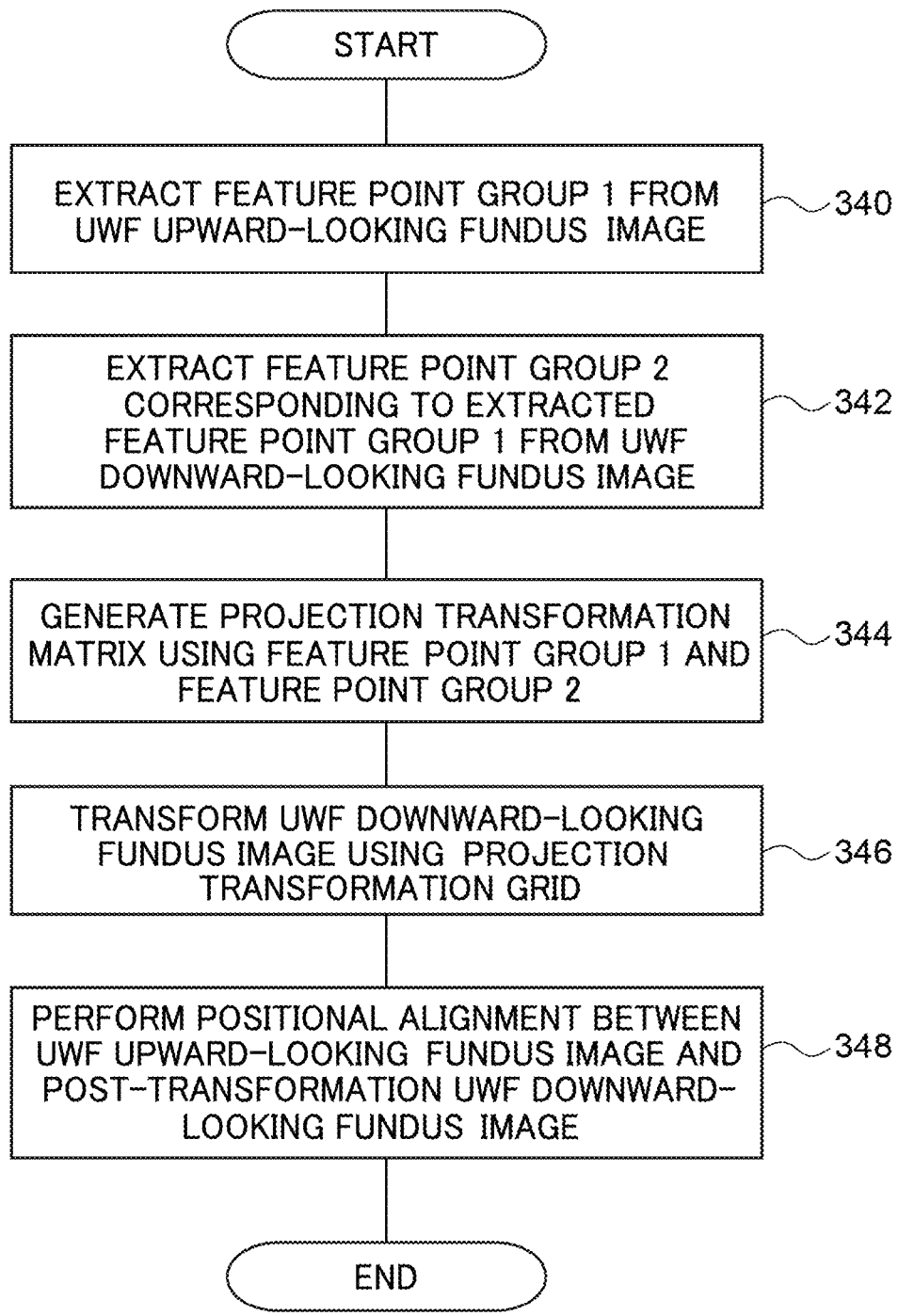

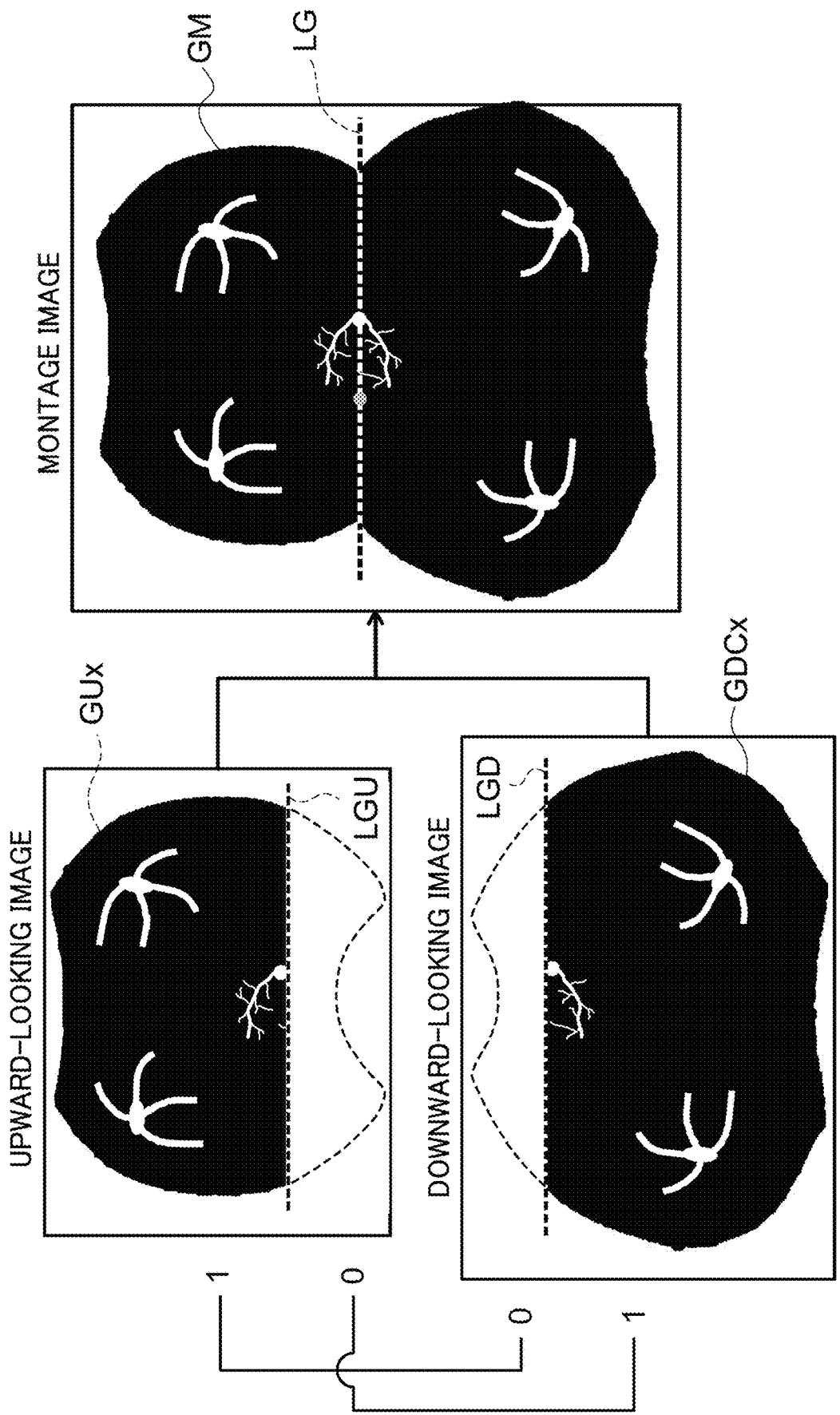

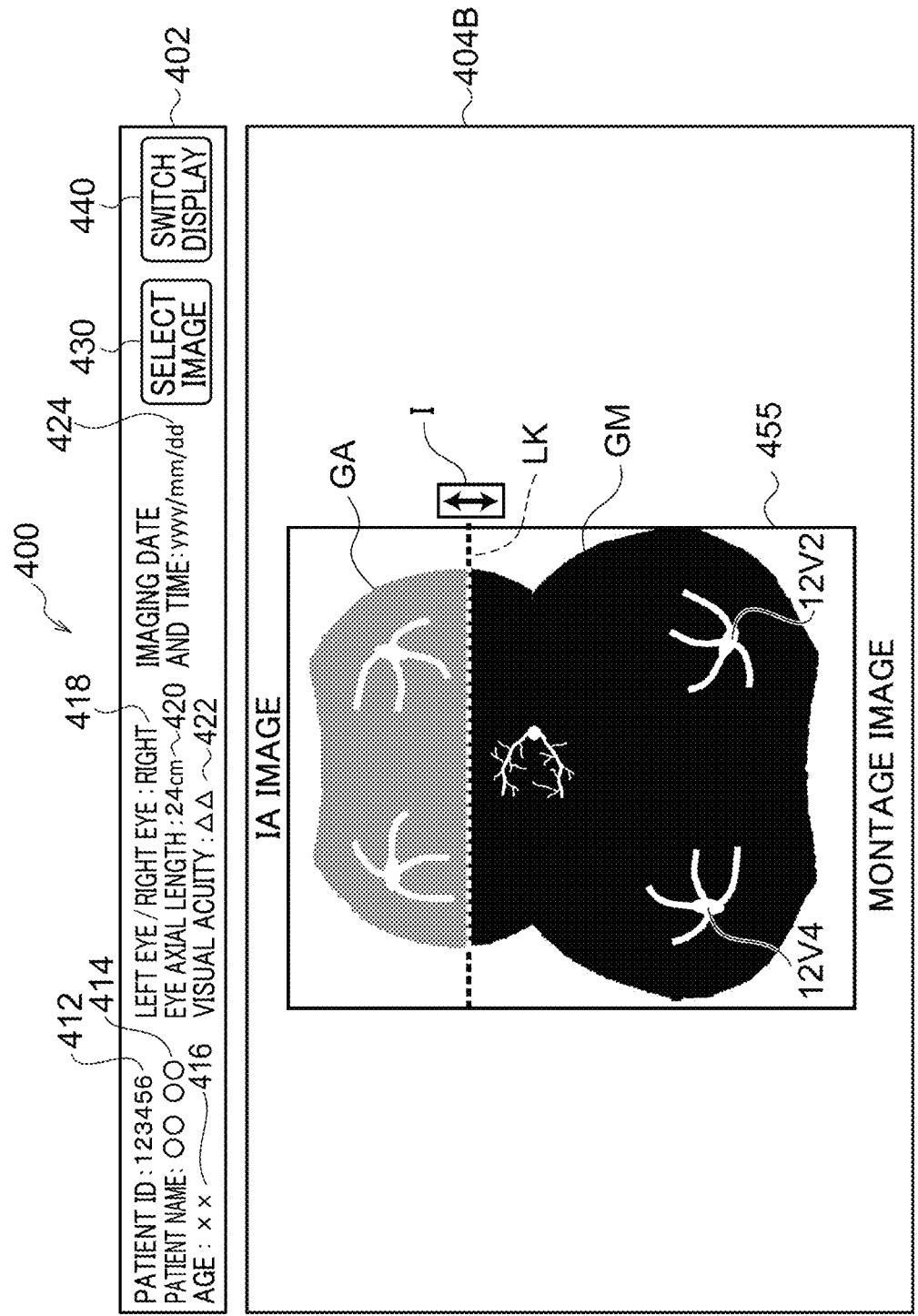

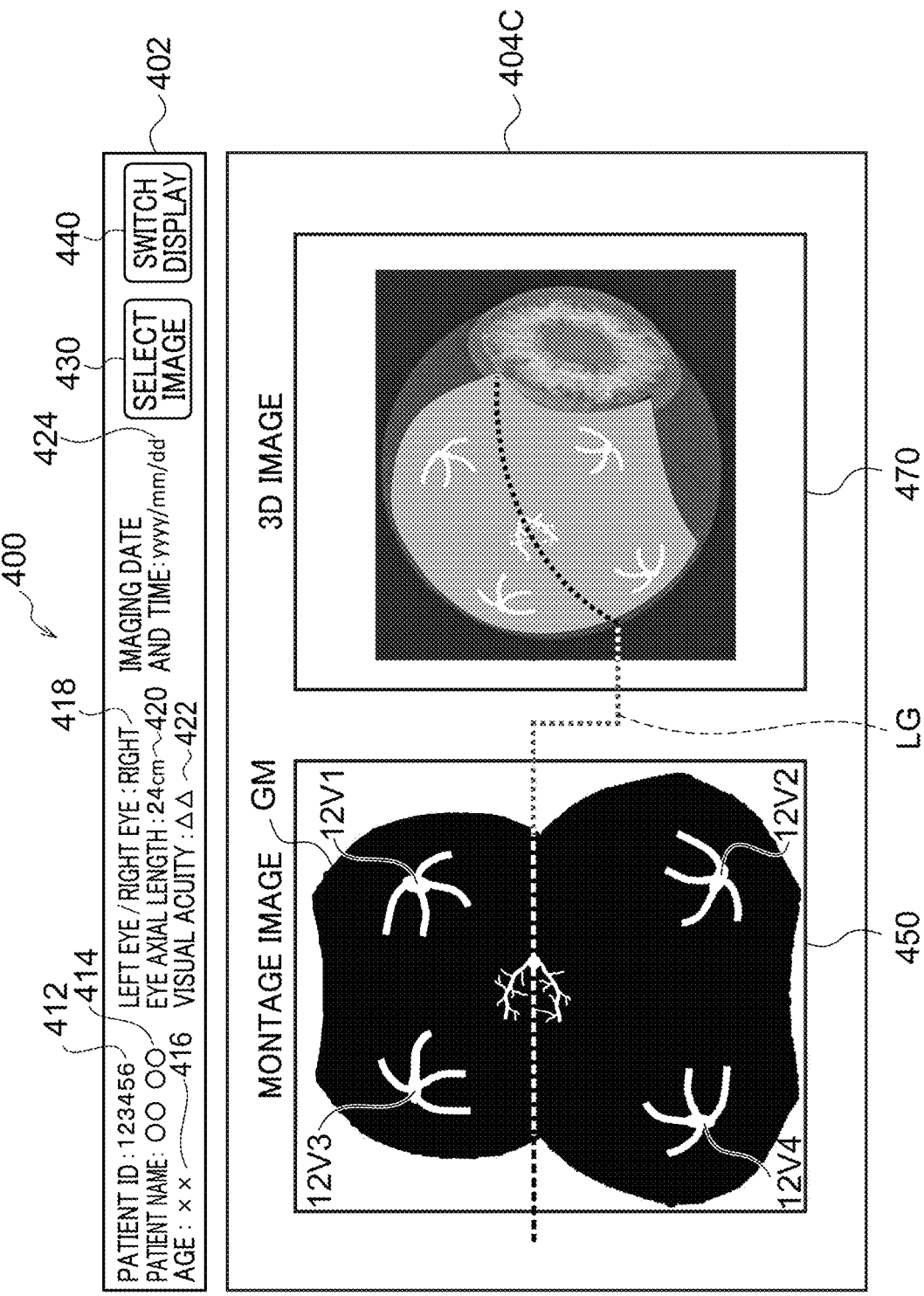

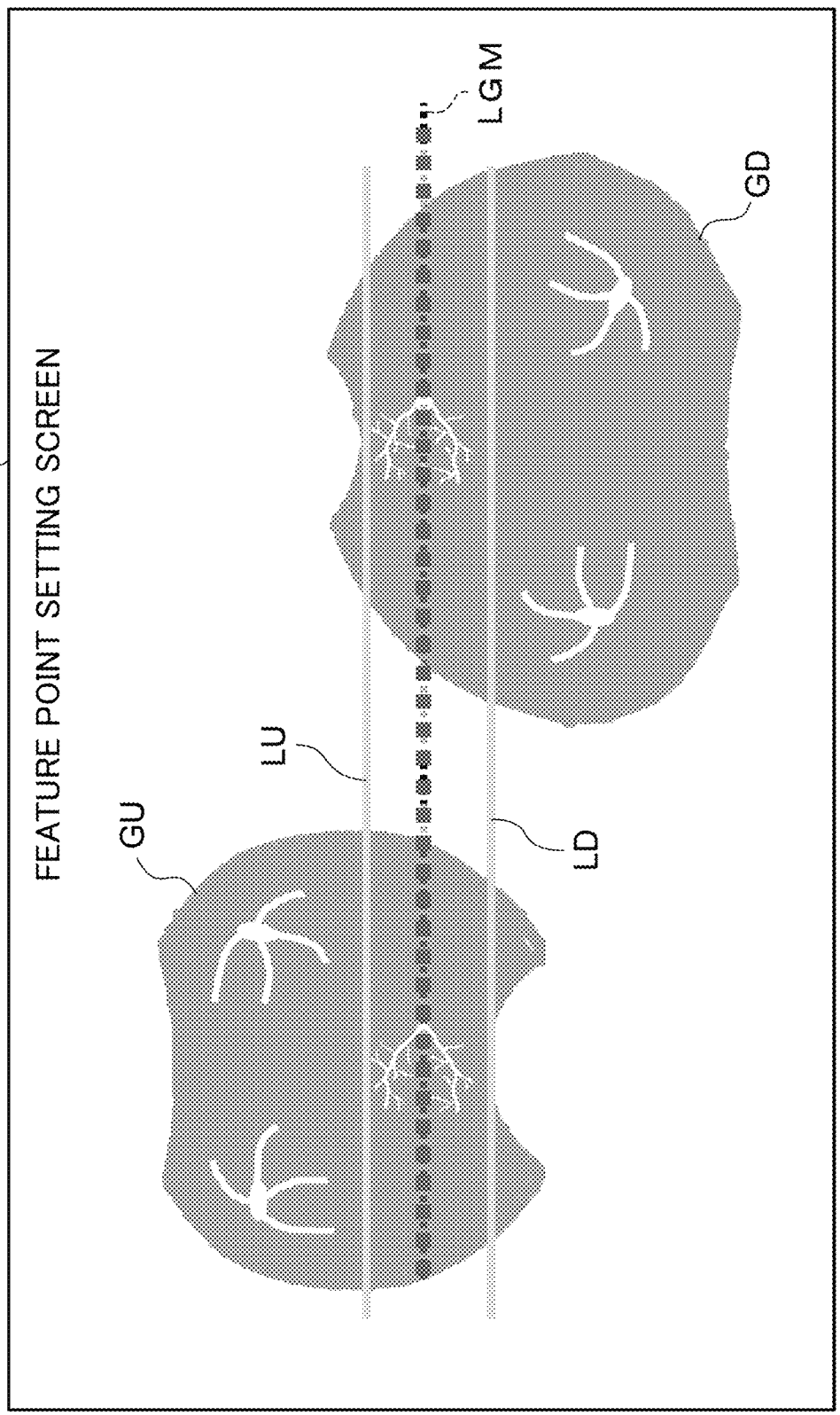

SYSTEMS AND METHODS FOR COMBINING FUNDUS IMAGES OF AN EYE

TECHNICAL FIELD

The present invention relates to an image processing method, an image processing device, and an image processing program.

BACKGROUND ART

US Patent Application Laid-Open No. 2009/0136100 discloses a device and method for synthesizing a panoramic fundus image. There remains demand for an effective image synthesizing method for analysis of structures in a fundus-peripheral portion.

SUMMARY OF INVENTION

An image processing method of a first aspect of technology disclosed herein includes acquiring a first direction fundus image imaged in a state in which an examined eye is directed in a first direction, and a second direction fundus image imaged in a state in which the examined eye is directed in a second direction different to the first direction, generating a combined image for analyzing a fundus-peripheral portion of the examined eye by combining the first direction fundus image and the second direction fundus image, and outputting the combined image.

An image processing device of a second aspect of technology disclosed herein includes an acquisition section configured to acquire a first direction fundus image imaged in a state in which an examined eye is directed in a first direction, and a second direction fundus image imaged in a state in which the examined eye is directed in a second direction different to the first direction, a generation section configured to generate a combined image for analyzing a fundus-peripheral portion of the examined eye by combining the first direction fundus image and the second direction fundus image, and an output section configured to output the combined image.

An image processing program of a third aspect of technology disclosed herein causes a computer to function as an acquisition section configured to acquire a first direction fundus image imaged in a state in which an examined eye is directed in a first direction, and a second direction fundus image imaged in a state in which the examined eye is directed in a second direction different to the first direction, a generation section configured to generate a combined image for analyzing a fundus-peripheral portion of the examined eye by combining the first direction fundus image and the second direction fundus image, and an output section configured to output the combined image.

BRIEF DESCRIPTION OF DRAWINGS

FIG. 2 is a schematic configuration diagram illustrating an overall configuration of an ophthalmic device 110.

FIG. 5 is a flowchart illustrating processing during image capture of the fundus of the examined eye 12 as executed by the CPU 22 of the ophthalmic device 110.

FIG. 11 is a flowchart illustrating positional alignment processing between images at step 324 in FIG. 10.

FIG. 13 is a diagram to explain generation of a montage image GM.

FIG. 15 is a diagram illustrating a second display mode of the display screen 400 of the display 256 of the viewer 150.

FIG. 16 is a diagram illustrating a third display mode of the display screen 400 of the display 256 of the viewer 150.

FIG. 17 is a diagram illustrating a fourth display mode of the display screen 400 of the display 256 of the viewer 150.

DESCRIPTION OF EMBODIMENTS

Detailed explanation follows regarding an exemplary embodiment of the present invention, with reference to the drawings.

Figure 1:
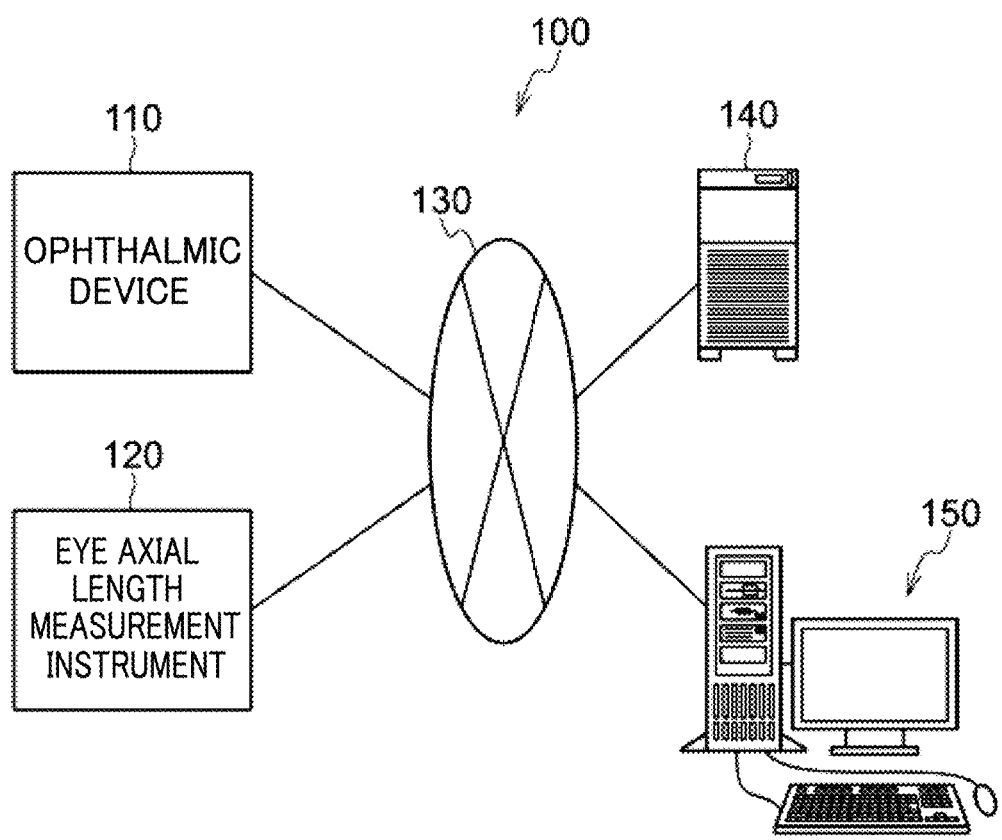
FIG. 1 is a block diagram illustrating an ophthalmic system 100.

Explanation follows regarding configuration of an ophthalmic system 100, with reference to FIG. 1. As illustrated in FIG. 1, the ophthalmic system 100 includes an ophthalmic device 110, an eye axial length measurement instrument 120, a server device (referred to hereafter as a "server") 140, and a display device (referred to hereafter as a "viewer") 150. The ophthalmic device 110 acquires images of a fundus. The eye axial length measurement instrument 120 measures the eye axial length of a patient. The server 140 stores plural fundus images and eye axial lengths obtained by imaging the fundi of plural patients with the ophthalmic device 110, in association with patient IDs. The viewer 150 displays fundus images and analysis results acquired from the server 140.

The server 140 is an example of an "image processing device" of technology disclosed herein.

The ophthalmic device 110, the eye axial length measurement instrument 120, the server 140, and the viewer 150 are connected together over a network 130.

Note that other ophthalmic equipment (examination equipment for measuring a field of view, measuring intraocular pressure, or the like) and/or a diagnostic support device that analyzes images using artificial intelligence (AI) may be connected to the ophthalmic device 110, the eye axial length measurement instrument 120, the server 140, and the viewer 150 over the network 130.

Next, explanation follows regarding configuration of the ophthalmic device 110, with reference to FIG. 2. As illustrated in FIG. 2, the ophthalmic device 110 includes a control unit 20, a display/operation unit 30, and a SLO unit 40. The ophthalmic device 110 images a posterior eye portion (fundus) of an examined eye 12. The ophthalmic device 110 may further include a non-illustrated OCT unit to acquire OCT data for the fundus. SLO is an acronym for Scanning Laser Ophthalmoscopy. OCT is an acronym standing for Optical Coherence Tomography.

The control unit 20 includes a computer provided with a CPU 22, memory 24, a communication interface (I/F) 26, and the like. The display/operation unit 30 is a graphical user interface that displays images obtained by imaging and also accepts various instructions, including imaging instructions, and includes a display 32 and an input/instruction device 34.

Figure 4:
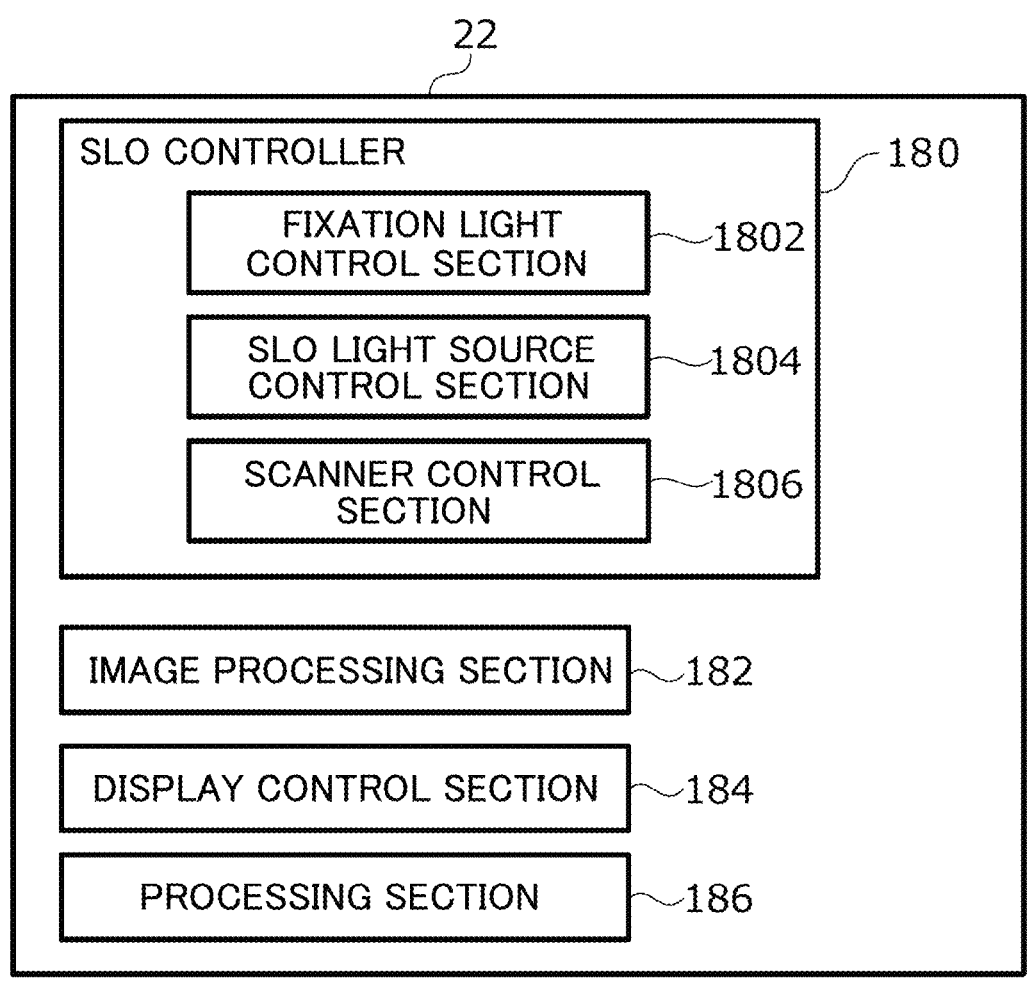
FIG. 4 is a block diagram illustrating functionality of a CPU 22 of the ophthalmic device 110.

The CPU 22 executes an image capture processing program so as, as illustrated in FIG. 4, to cause the CPU 22 to function as a SLO controller 180 (including a fixation light control section 1802, an SLO light source control section 1804, and a scanner control section 1806), an image processing section 182, a display control section 184, and a processing section 186.

The memory 24 is stored with the image capture processing program used to perform image capture processing when imaging the fundus of the examined eye 12, as described later.

The SLO unit 40 includes a G light source 42 (green light: wavelength 530 nm), a R light source 44 (red light: wavelength 650 nm), and an IR light source 46 (infrared radiation (near-infrared light), wavelength 800 nm). The respective light sources 42, 44, 46 emit light in response to commands from the control unit 20. Note that the light sources 42, 44, 46 may employ LED light sources or laser light sources. Note that explanation follows regarding an example in which laser light sources are employed.

The SLO unit 40 includes optical systems 50, 52, 54, 56 that either reflect or transmit the light from the light sources 42, 44, 46 so as to guide the light onto a single light path. The optical systems 50, 56 are configured by mirrors, whereas the optical systems 52, 54 are configured by beam splitters, specifically dichroic mirrors, half-mirrors, or the like.

The G light is reflected by the optical systems 50, 54, the R light is transmitted through the optical systems 52, 54, and the IR light is reflected by the optical systems 52, 56, such that the G light, the R light, and the IR light are each guided onto a single light path.

The SLO unit 40 includes a wide-angle optical system 80 that scans the light from the light sources 42, 44, 46 across the posterior eye portion (fundus) of the examined eye 12 in a two-dimensional pattern. The SLO unit 40 includes a beam splitter 58 that, out of the light from the posterior eye portion (fundus) of the examined eye 12, reflects G light and transmits light other than the G light. The SLO unit 40 also includes a beam splitter 60 that, out of the light transmitted through the beam splitter 58, reflects R light and transmits light other than the R light. The SLO unit 40 also includes a beam splitter 62 that, out of the light transmitted through the beam splitter 60, reflects IR light. Dichroic mirrors, half-mirrors, or the like may be employed as the beam splitters 58, 60, 62.

The SLO unit 40 includes a G light detection element 72 that detects the G light reflected by the beam splitter 58, a R light detection element 74 that detects the R light reflected by the beam splitter 60, and an IR light detection element 76 that detects the IR light reflected by the beam splitter 62. For example, avalanche photodiodes (APDs) may be employed as the light detection elements 72, 74, 76.

Moreover, the SLO unit 40 includes a fixation target control device 90 that is controlled by the control unit 20 so as to illuminate an upper fixation light 92U and a lower fixation light 92D (as well as a non-illustrated central fixation light). The orientation (gaze direction) of the examined eye 12 can be changed by illuminating the central fixation light, the upper fixation light 92U, and the lower fixation light 92D respectively.

The wide-angle optical system 80 includes an X direction scanning device 82 configured by polygonal mirrors so as to scan the light from the light sources 42, 44, 46 in an X direction, a Y direction scanning device 84 configured by mirror galvanometers so as to scan the light from the light sources 42, 44, 46 in a Y direction, and an optical system 86 configured by a lens system made up of a concave mirror such as an elliptical mirror and plural lenses so as to illuminate an Ultra-Wide Field (UWF) with the scanned light. The respective scanning devices of the X direction scanning device 82 and the Y direction scanning device 84 may employ Micro Electro Mechanical System (MEMS) mirrors. Alternatively, instead of providing separate scanners for the X direction and the Y direction, a single MEMS mirror may be configured capable of two-dimensional scanning. Note that in cases in which the ophthalmic device 110 is installed on a horizontal plane, the X direction corresponds to a horizontal direction, and the Y direction corresponds to a direction perpendicular to the horizontal plane. A direction connecting the center of the pupil at an anterior eye portion of the examined eye 12 and the center of the eyeball of the examined eye 12 is referred to as a Z direction. The X direction, the Y direction, and the Z direction are therefore mutually perpendicular to one another.

The wide-angle optical system 80 has an ultra-wide angle Field of View (FOV) with respect to the fundus, and is capable of imaging a region spanning from a posterior pole of the fundus and crossing an equatorial portion of the examined eye 12.

Figure 3A:
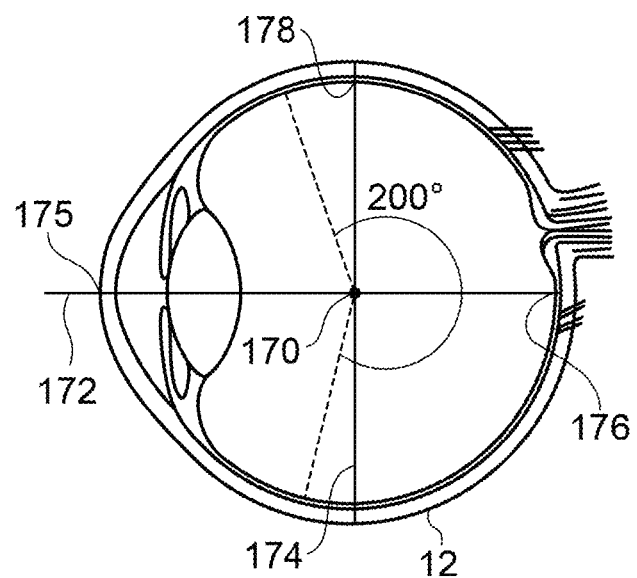
FIG. 3A is a first diagram to illustrate an imaging range of a fundus of an examined eye 12 by the ophthalmic device 110.

Explanation follows regarding an equatorial portion 178, with reference to FIG. 3A. The eyeball (examined eye 12) is a spherical structure with a diameter of approximately 24 mm and an eyeball center 170. A straight line joining an anterior pole 175 to a posterior pole 176 is referred to as an ocular axis 172, a line running along an intersection between a plane orthogonal to the ocular axis 172 and the eyeball surface is referred to as a line of latitude, and an equator 174 corresponds to the line of latitude with the greatest length. Portions of the retina and the choroid coinciding with the position of the equator 174 configure the equatorial portion 178. The equatorial portion 178 corresponds to one part of a fundus-peripheral portion.

The ophthalmic device 110 is capable of imaging a region covered by an internal irradiation angle of 200° with respect to the position of the eyeball center 170 of the examined eye 12. Note that an internal irradiation angle of 200° corresponds to an external irradiation angle of 167° relative to the pupil of the eyeball of the examined eye 12. Namely, the wide-angle optical system 80 irradiates laser light through the pupil at an angle of view corresponding to an external irradiation angle of 167° in order to image a fundus region over an internal irradiation angle of 200°.

Figure 3B:
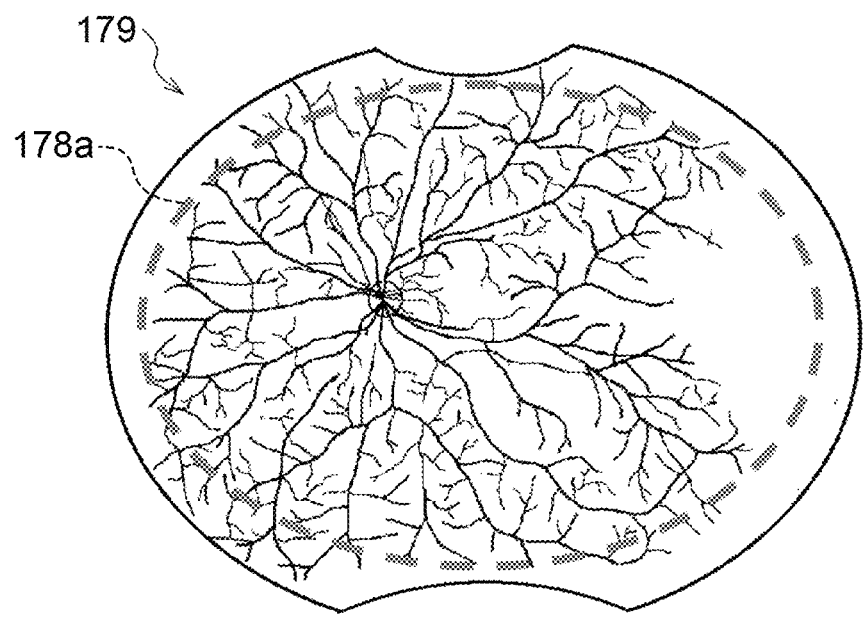
FIG. 3B illustrates an image of a fundus obtained by the ophthalmic device 110, and is a second diagram to illustrate an imaging range of the fundus of the examined eye 12 by the ophthalmic device 110.

FIG. 3B illustrates an SLO image 179 obtained by imaging with the ophthalmic device 110 that is capable of scanning over an internal irradiation angle of 200°. As illustrated in FIG. 3B, the equatorial portion 178 corresponds to an internal irradiation angle of 180°, and the location indicated by the dotted line 178a in the SLO image 179 corresponds to the equatorial portion 178. In this manner, the ophthalmic device 110 is capable of imaging a fundus-peripheral region spanning from a posterior pole portion including the posterior pole 176 and crossing the equatorial portion 178 in a single take (either a single image or a single scan). Namely, the ophthalmic device 110 is capable of capturing from a central portion of the fundus to a peripheral portion of the fundus in a single take. The ophthalmic device 110 is an example of an "imaging device" of technology disclosed herein.

Figure 3C:
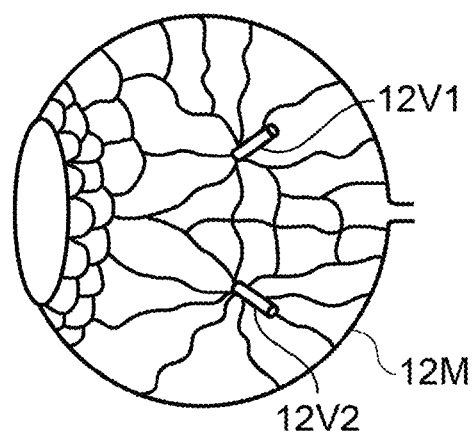
FIG. 3C is a third diagram to illustrate an imaging range of the fundus of the examined eye 12 by the ophthalmic device 110.

FIG. 3C is a diagram illustrating a positional relationship between a choroid 12M and vortex veins 12V1, 12V2 of the eyeball.

In FIG. 3C, choroid blood vessels of the choroid 12M are illustrated in a mesh pattern. The choroid blood vessels carry blood around the entire choroid. Blood flows out from the eyeball through plural (usually from four to six) vortex veins of the examined eye 12. FIG. 3C illustrates an upper vortex vein V1 and a lower vortex vein V2 present on one side of the eyeball. Vortex veins are frequently present in the vicinity of the equatorial portion 178. Accordingly, the ophthalmic device 110 that is capable of scanning the fundus-peripheral portion over a broad range with an internal irradiation angle of 200° as described above is employed in order to image the vortex veins and the choroid blood vessels peripheral to the vortex veins in the examined eye 12.

An SLO fundus image obtained by imaging the examined eye 12 using the ophthalmic device 110 that is capable of scanning over an internal irradiation angle of 200° is referred to as a UWF fundus image.

The configuration of the ophthalmic device 110 provided with the wide-angle optical system as described above may employ the configuration described in International Application No. PCT/EP 2017/075852. The disclosure of International Application No. PCT/EP 2017/075852 (International Publication No. WO2018/069346), filed internationally on Oct. 10, 2017, is incorporated in its entirety by reference herein.

Explanation follows regarding imaging of upward-looking and downward-looking UWF fundus images using the ophthalmic device 110.

First, the input/instruction device 34 is used to input the ophthalmic device 110 with information including patient attribute information such as a patient ID and patient name, as well as information to indicate whether the examined eye to be imaged is a left eye or a right eye. If the patient has existing medical records, patient attribute information recorded in the server 140 is read when the patient ID is input.

Next, the ophthalmic device 110 displays on the display 32 a menu screen to prompt selection of either a normal imaging mode in which the central fixation light is illuminated and the fundus is imaged over a broad range, or a montage image capture mode used to analyze structures in a fundus-peripheral portion (for example including vortex veins and choroid blood vessels in the vicinity of the vortex veins). Using the input/instruction device 34, a user is able to select the mode using the menu screen displayed on the display 32.

When the user selects the montage image capture mode, the CPU 22 of the ophthalmic device 110 executes the image capture processing program in order to implement image capture processing as illustrated by the flowchart in FIG. 5.

When the user has selected the montage image capture mode, the SLO controller 180 performs alignment and focus adjustment.

Figure 6A:
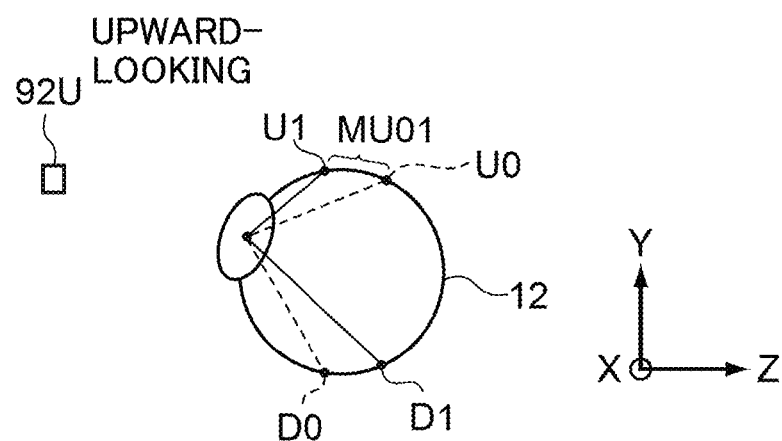
FIG. 6A is a diagram of a plane running parallel to an up-down direction and passing through a pupil and an eyeball center to illustrate an imaging range (spanning between U1 and D1) of a fundus in a case in which an optical axis of the examined eye 12 is directed in an oblique upward direction relative to the ophthalmic system 100.

At step 302 in FIG. 5, the fixation light control section 1802 controls the fixation target control device 90 so as to illuminate the upper fixation light 92U in order to direct the gaze of the patient in an oblique upward direction. As illustrated in FIG. 6A, the gaze of the patient is thus directed in the oblique upward direction, namely a direction running from the eyeball center toward the upper fixation light 92U. In addition to illuminating the upper fixation light 92U, the operator of the ophthalmic device 110 may also give an instruction such as "please look upward" to direct the gaze of the patient in the oblique upward direction and thereby achieve a state in which the gaze of the examined eye is directed in the oblique upward direction The oblique upward direction is an example of a "first direction" of technology disclosed herein.

At step 304, the fundus is imaged in an upward-looking state, in which the gaze of the patient is directed in the oblique upward direction. Specifically, the SLO light source control section 1804 causes the G light source 42 and the R light source 44 to emit G light and R light respectively. The scanner control section 1806 controls the X direction scanning device 82 and the Y direction scanning device 84. The G light and the R light scanned in the X direction and the Y direction are reflected by the fundus of the examined eye.

Since a G light, which wavelength corresponds to green light, is reflected by the retina, structural information relating to the retina is included. The G light reflected from the examined eye 12 is detected by the G light detection element 72. The image processing section 182 generates image data for a UWF upward-looking fundus image G based on a signal from the G light detection element 72. Similarly, R light reflected from the examined eye 12 is detected by the R light detection element 74. Since red laser light (R light) is reflected at the choroid, this being deeper than the retina, structural information relating to the choroid is included. The image processing section 182 generates image data for a UWF upward-looking fundus image R based on a signal from the R light detection element 74. The image processing section 182 then generates image data for a UWF upward-looking fundus image RG by combining the UWF upward-looking fundus image and the UWF upward-looking fundus image R at a predetermined mixing ratio.

Note that the UWF upward-looking fundus image G, the UWF upward-looking fundus image R, and the UWF upward-looking fundus image RG are referred to collectively as UWF upward-looking fundus images when not drawing a distinction therebetween.

The UWF upward-looking fundus images are examples corresponding to a "first direction fundus image" of technology disclosed herein.

When the fundus is imaged in a state in which the optical axis of the ophthalmic system 100 aligns with the optical axis of the examined eye 12, a UWF en face fundus image of the fundus of the examined eye 12 thus obtained captures a region spanning between an upper position U0 and a lower position D0 of the fundus in the Y-Z plane illustrated in FIG. 6A.

Figure 7A:
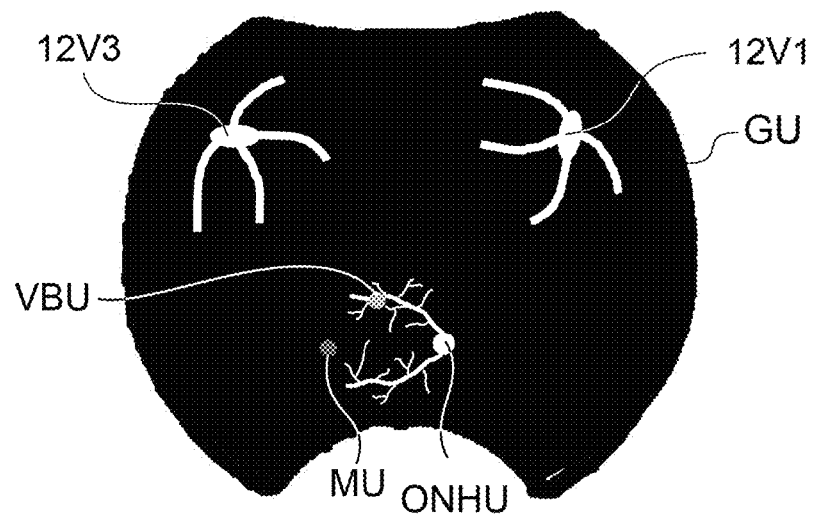
FIG. 7A is a diagram illustrating a UWF upward-looking fundus image GU obtained by upward-looking imaging at step 304 in FIG. 5.

The upward-looking fundus images are obtained by imaging the fundus while looking upward. As illustrated in FIG. 6A, due to the gaze of the patient being directed in the oblique upward direction, each upward-looking fundus image corresponds to an image of a region spanning between an upper position U1 above the upper position U0, and a lower position D1. Accordingly, each upward-looking fundus image includes an image of a region MU01 that is not included in the en face image. FIG. 7A illustrates a UWF upward-looking fundus image for a right eye. This UWF upward-looking fundus image GU includes a vortex vein 12V1 on the nose side (on the right side of the drawing) and a vortex vein 12V3 on the ear side (on the left side of the drawing), the vortex veins 12V1 and 12V3 being present in the vicinity of an eyeball upper side of the equatorial portion, positioned toward the upper side of the UWF upper side fundus image GU. Moreover an optical nerve head ONH and a macula M present in a fundus central portion are positioned toward the lower side of the UWF upper side fundus image GU.

Figure 6B:
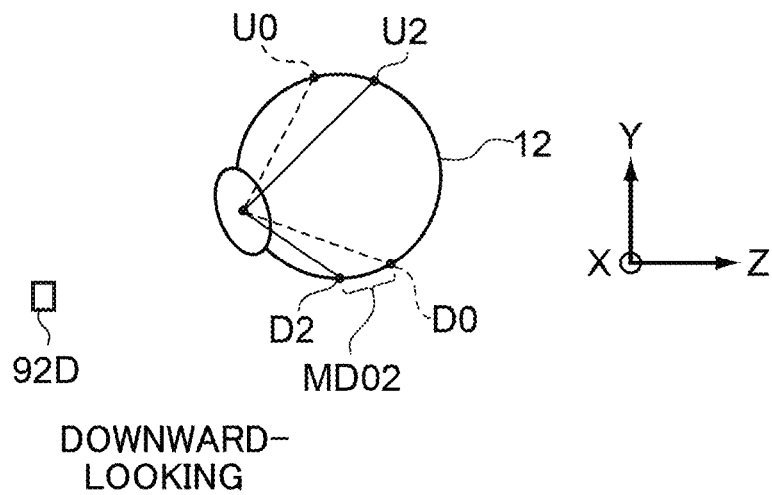
FIG. 6B is a diagram of a plane running parallel to an up-down direction and passing through the pupil and the eyeball center to illustrate an imaging range (spanning between U2 and D2) of a fundus in a case in which the optical axis of the examined eye 12 is directed in an oblique downward direction relative to the ophthalmic system 100.

At step 306, the fixation light control section 1802 controls the fixation target control device 90 so as to illuminate the lower fixation light 92D in order to direct the gaze of the patient in an oblique downward direction. As illustrated in FIG. 6B, the gaze of the patient is thus directed in the oblique downward direction, namely a direction running from the eyeball center toward the lower fixation light 92D. In addition to illuminating the upper fixation light 92D, the operator of the ophthalmic device 110 may also give an instruction such as "please look downward" to direct the gaze of the patient in the oblique downward direction and thereby achieve a state in which the gaze of the examined eye is directed in the oblique downward direction.

The oblique downward direction is an example of a "second direction" of technology disclosed herein.

At step 308, the fundus is imaged in a downward-gazing state, in which the gaze of the patient is directed in the oblique downward direction. Similarly to at step 304, the SLO light source control section 1804 causes the G light source 42 and the R light source 44 to emit G light and R light respectively. The scanner control section 1806 controls the X direction scanning device 82 and the Y direction scanning device 84 so as to scan the G light and the R light in the X direction and the Y direction. Similarly to at step 304, the image processing section 182 generates image data for a UWF downward-looking fundus image G, a UWF downward-looking fundus image R, and a UWF downward-looking fundus image RG.

Note that the UWF downward-looking fundus image G, the UWF downward-looking fundus image R, and the UWF downward-looking fundus image RG are referred to collectively as UWF downward-looking fundus images when not drawing a distinction therebetween.

The UWF downward-looking fundus images are an example of a "second direction fundus image" of technology disclosed herein.

Figure 7B:
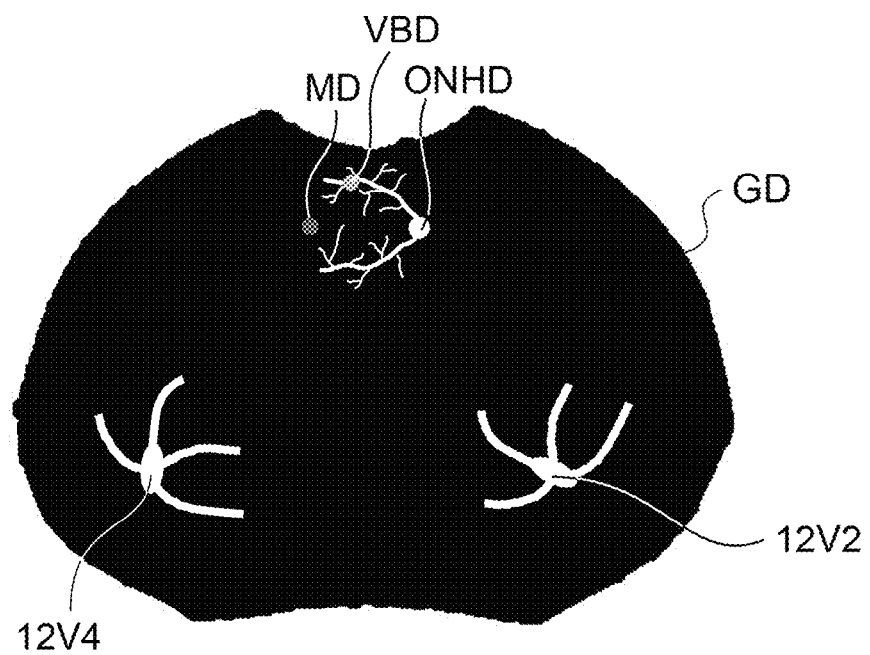
FIG. 7B is a diagram illustrating a UWF downward-looking fundus image GD obtained by downward-looking imaging at step 308 in FIG. 5.

The downward-looking fundus images are obtained by imaging the fundus while looking downward. As illustrated in FIG. 6B, due to the gaze of the patient being directed in the oblique downward direction, each downward-looking fundus image corresponds to an image of a region spanning between a lower position D2 below the lower position D0 and an upper position U2. Accordingly, each downward-looking fundus image includes an image of a region MD02 that is not included in the UWF en face fundus image. FIG. 7B illustrates a UWF downward-looking fundus image GD for a right eye. This UWF downward-looking fundus image GD includes a vortex vein 12V2 on the nose side (on the right side of the drawing) and a vortex vein 12V4 on the ear side (on the left side of the drawing), the vortex veins 12V2 and 12V4 being present in the vicinity of the equatorial portion at the eyeball upper side thereof, positioned toward the lower side of the UWF downward-looking fundus image GD. An optical nerve head ONH and a macula M present in a fundus central portion are positioned toward the upper side of the UWF downward-looking fundus image GD.

At step 310, the processing section 186 transmits image data for the UWF upward-looking fundus images and the UWF downward-looking fundus images to the server 140 via the communication interface (I/F) 26. The processing section 186 also transmits the patient ID and the patient attribute information (patient name, age, information indicating whether each fundus image corresponds to a left eye or a right eye, visual acuity, imaging date and time, and the like) to the server 140 when transmitting the image data to the server 140.

The server 140 stores the received image data, patient ID, and patient attribute information in association with each other in a storage device 254, described later.

Note that the display control section 184 may display the UWF upward-looking fundus images and the UWF downward-looking fundus images on the display 32.

When the user has selected the normal imaging mode, in which the fundus is imaged over a broad range while looking straight ahead, the SLO controller 180 performs alignment and focus adjustment. The fixation light control section 1802 then controls the fixation target control device 90 so as to illuminate the central fixation light. The gaze of the patient is thus fixed straight ahead, and a UWF en face fundus image such as that illustrated in FIG. 3B is imaged.

In cases in which UWF en face fundus images have been acquired, at step 310 the processing section 186 transmits image data of the UWF en face fundus images in a similar manner to that described above.

Note that similarly to the UWF upward-looking fundus images and the UWF downward-looking fundus images, the UWF en face fundus images generated include a UWF en face fundus image G, a UWF en face fundus image R, and a UWF en face fundus image RG.

In order to analyze structures in the fundus-peripheral portion (for example vortex veins and choroid blood vessels in the vicinity of the vortex veins), it is necessary to image a fundus region including the periphery of the equatorial portion and crossing the equatorial portion in the direction of the anterior eye portion. During wide-angle imaging performed while looking straight ahead, the eyelids and eyelashes of the examinee, as well as casing of the ophthalmic device 110 may enter the image, with the result that the fundus-peripheral portion cannot be imaged. In such cases, it would not be possible to image the vortex veins and the choroid blood vessels in the vicinity of the vortex veins, with the result that an image including all of the vortex veins in the fundus-peripheral portion or peripheral to the equatorial portion cannot be acquired.

Accordingly, in the present exemplary embodiment the UWF upward-looking fundus image GU is acquired in a state in which the gaze of the patient is directed upward and the UWF downward-looking fundus image GD is acquired in a state in which the gaze of the patient is directed downward. These two images are then combined in order to generate a montage image, thereby reliably capturing a broader region than that captured in a single UWF en face fundus image. Employing a montage image in this manner enables a montage image to be obtained including vortex veins and choroid blood vessels in the vicinity of the vortex veins, from which the eyelids and eyelashes of the examinee, as well as any casing of the ophthalmic device 110 have been removed. Such a montage image is well-suited to the detection of pathological lesions and above regions in the fundus-peripheral portion, as well as the detection of vortex veins and choroid blood vessels in the vicinity of the vortex veins.

Explanation follows regarding generation of a montage image by the server 140.

Figure 8:
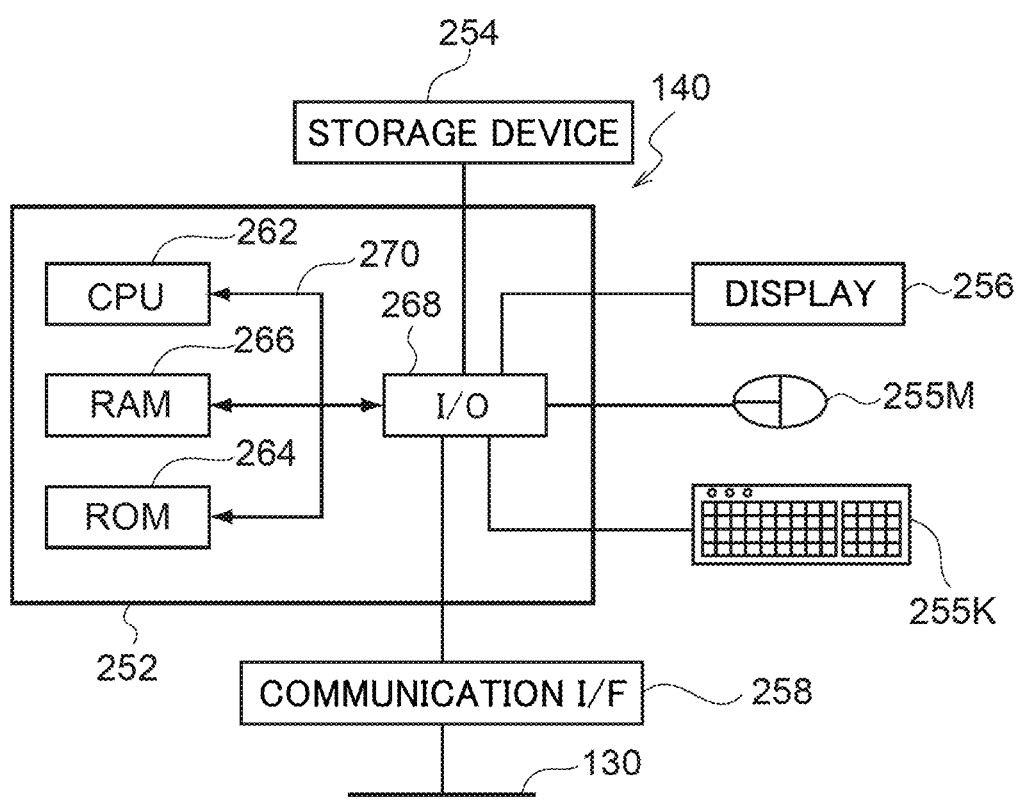
FIG. 8 is a block diagram illustrating an electrical configuration of a server 140.

Explanation follows regarding configuration of the server 140, with reference to FIG. 8. As illustrated in FIG. 8, the server 140 includes a computer unit 252. The computer unit 252 includes a CPU 262, RAM 266, ROM 264, and an input/output (I/O) port 268. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 via the communication interface (I/F) 258. Accordingly, the server 140 is capable of communicating with the ophthalmic device 110, the eye axial length measurement instrument 120, and the viewer 150. The storage device 254 is stored with a montage image creation processing program, described later. Note that the montage image creation processing program may be stored in the ROM 264.

The montage image creation processing program is an example of an "image processing program" of technology disclosed herein.

Figure 9:
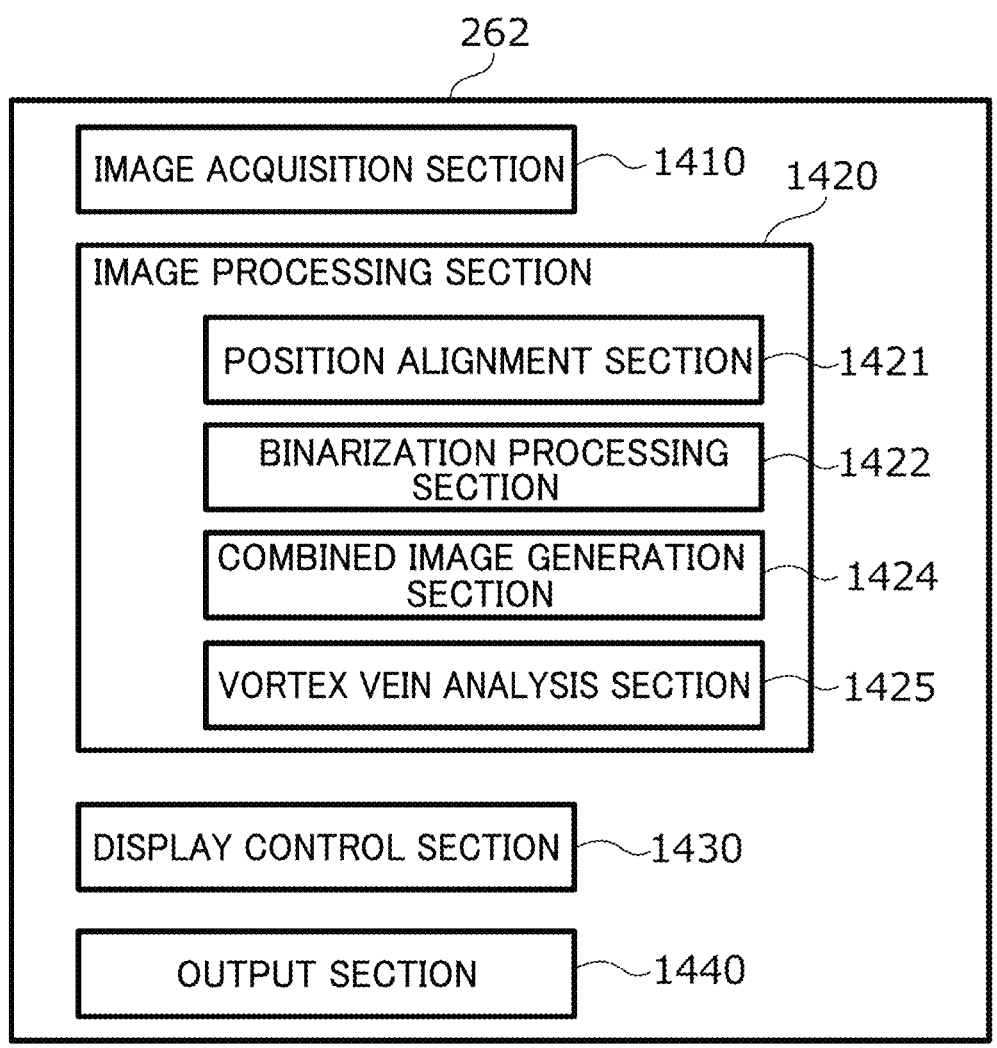
FIG. 9 is a block diagram illustrating functionality of a CPU 262 of the server 140.

The CPU 262 of the server 140 executes the montage image creation processing program so as to cause the CPU 262 to function as an image acquisition section 1410, an image processing section 1420 (including a position alignment section 1421, a binarization processing section 1422, a combined image generation section 1424, and a vortex vein analysis section 1425), a display control section 1430, and an output section 1440, as illustrated in FIG. 9.

The image acquisition section 1410 is an example of an "acquisition section" of technology disclosed herein. The image processing section 1420 is an example of a "generation section" of technology disclosed herein. The output section 1440 is an example of an "output section" of technology disclosed herein.

Figure 10:
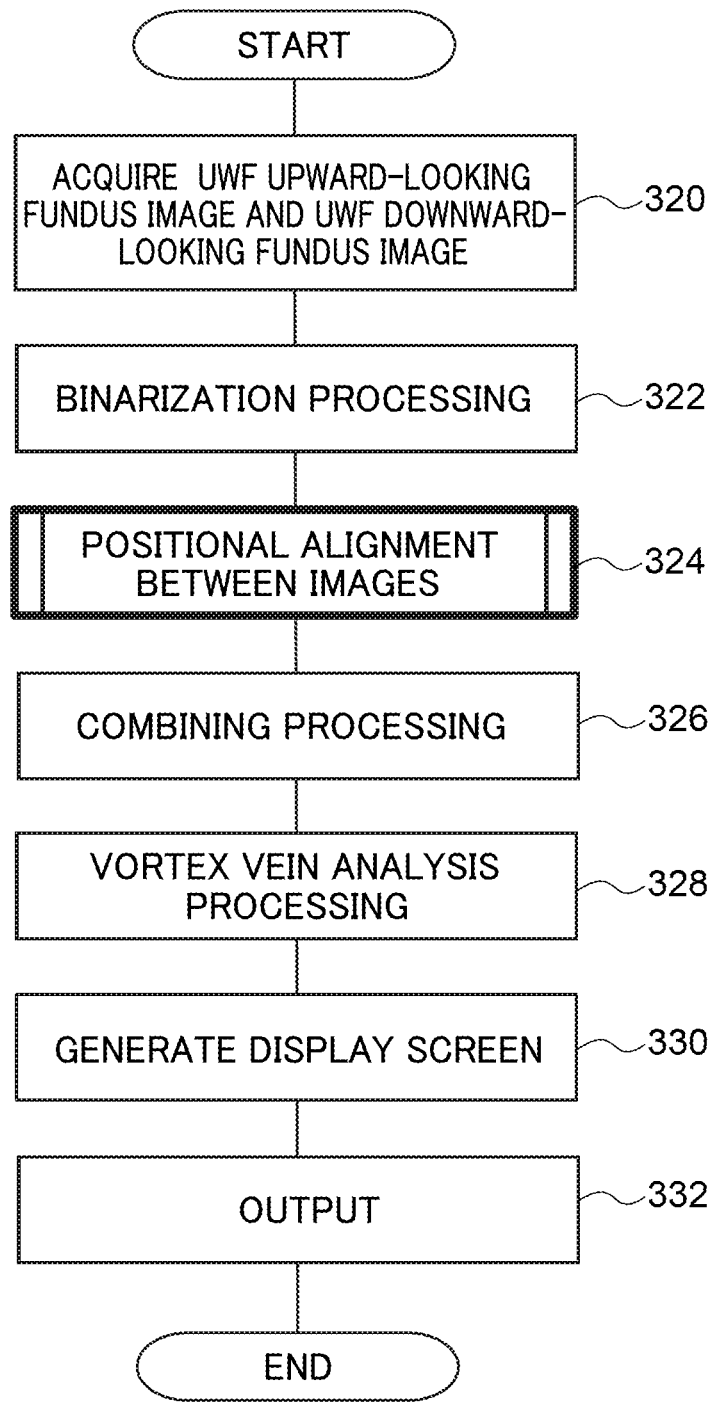
FIG. 10 is a flowchart illustrating montage image creation processing executed by the CPU 262 of the server 140.

Next, detailed explanation follows regarding montage image creation processing executed by the CPU 262 of the server 140, with reference to FIG. 10. The CPU 262 of the server 140 executes the montage image creation processing program in order to implement the montage image creation processing illustrated by the flowchart in FIG. 10.

The montage image creation processing is an example of an "image processing method" of technology disclosed herein.

A user (for example an ophthalmologist) turns on a non-illustrated montage image display button in order to instruct display on the viewer 150 of a fundus image (montage image) of the examined eye 12 of a patient for the purpose of diagnosing the examined eye 12. When this is performed, the operator inputs the patient ID to the viewer 150. The viewer 150 then outputs montage image creation instruction data to the server 140 together with the patient ID. Having received the montage image creation instruction data and the patient ID, the server 140 executes the montage image creation processing program.

Note that the montage image creation processing program may be executed at the point in time when UWF upward-looking fundus images and UWF downward-looking fundus images imaged by the ophthalmic device 110 are transmitted to the server 140.

At step 320 in the flowchart of FIG. 10, the image acquisition section 1410 acquires the UWF upward-looking fundus images and the UWF downward-looking fundus images from the storage device 254. At step 322, the binarization processing section 1422 performs processing to emphasize blood vessels in the UWF upward-looking fundus images and the UWF downward-looking fundus images. The binarization processing section 1422 then executes binarization processing so as to perform binarization about a predetermined threshold value. Blood vessels of the fundus are emphasized in white as a result of the binarization processing.

At step 324, the position alignment section 1421 performs positional alignment between the UWF upward-looking fundus images and the UWF downward-looking fundus images. Explanation follows regarding positional alignment processing performed at step 324, with reference to the flowchart of FIG. 11. Here, explanation will be given regarding a case in which the UWF downward-looking fundus images are transformed with reference to the UWF upward-looking fundus images (namely, a case in which only the UWF downward-looking fundus images are transformed, and the UWF upward-looking fundus images are not transformed).

At step 340 in FIG. 11, the position alignment section 1421 performs image processing to extract a feature point group 1 from the UWF upward-looking fundus image GU. As illustrated in FIG. 7A, the feature point group 1 includes plural feature points in the fundus image, including the optical nerve head ONHU, a macula MU, and a retinal blood vessel junction VBU. Note that a junction between choroid blood vessels may also be extracted as a feature point. The position alignment section 1421 extracts only structural information regarding the choroid from the UWF upward-looking fundus image G that includes structural information relating to the retina and the UWF upward-looking fundus image R that includes structural information relating to the choroid, by removing the structural information relating to the retina from the UWF upward-looking fundus image R. The position alignment section 1421 then extracts a retinal blood vessel junction from the UWF upward-looking fundus image G, and extracts a choroid blood vessel junction from the structural information relating only to the choroid. The respective feature points are configured by the pixel with the maximum brightness in an optical nerve head ONHU region, the pixel with the minimum brightness in a macula MU region, and pixels positioned at retinal blood vessel junctions and choroid blood vessel junctions. Coordinates of these pixels are extracted as feature point data. In addition to retinal blood vessel junctions and choroid blood vessel junctions, a region including a distinctive blood vessel layout pattern may be extracted and the central point of the region including this pattern then taken as a feature point.

Note that terminal points, bend points, or meander points of retinal blood vessels and choroid blood vessels may also be extracted as feature points.

Feature point detection algorithms such as Scale Intevariant Feature Transform (SIFT) or Speed Upped Robust Feature (SURF) may be employed in the processing relating to the feature points.

In order to perform positional alignment at high precision, preferably at least four of the feature points are extracted. The UWF upward-looking fundus image GU includes only a single optical nerve head and a single macula of the examined eye. Four or more feature points can therefore be extracted from the UWF upward-looking fundus image GU by extracting two or more junctions VBU of retinal blood vessels and choroid blood vessels.

The optical nerve head, macula, retinal blood vessels, and choroid blood vessels present in the fundus central portion are captured in both the UWF upward-looking fundus image GU and the UWF downward-looking fundus image GD, and therefore make suitable selection targets for feature points to be used in positional alignment. Namely, it is preferable to select feature points from the fundus central portion that configures a common region present in both the UWF upward-looking fundus image GU and the UWF downward-looking fundus image GD.

At step 340, the position alignment section 1421 extracts the feature point group 1 by performing image processing on the fundus central portion, namely a region at the lower side of the center of the UWF upward-looking fundus image GU.

The vortex veins 12V1 and 12V3 that are present in the fundus-peripheral portion and that appear in the UWF upward-looking fundus image GU are eliminated from selection as feature points. Since this fundus-peripheral portion is not a region common to both the UWF upward-looking fundus image GU and the UWF downward-looking fundus image GD, structures in this fundus-peripheral portion are eliminated from selection as feature points.

At step 342, the position alignment section 1421 extracts a feature point group 2 corresponding to the feature point group 1 from the UWF downward-looking fundus image GD. As illustrated in FIG. 7B, the feature point group 2 includes the optical nerve head ONHD and the macula MD, as well as a retinal blood vessel junction VBD. Since the eye is the same eye in both cases, the optical nerve head ONHD corresponds to the optical nerve head ONHU, and the macula MD corresponds to macula MU. The junction VBD corresponds to the blood vessel junction VBU, and a junction location exhibiting the same junction pattern as the junction pattern of the junction VBU is extracted using image recognition processing or the like.

At step 344, the position alignment section 1421 employs the feature point group 1 and the feature point group 2 to generate a projection transformation grid to geometrically transform the UWF downward-looking fundus image GD. The projection transformation grid is a grid used to map the UWF downward-looking fundus image GD onto the UWF upward-looking fundus image GU. The projection transformation grid is set using at least four feature points.

Figure 12A:
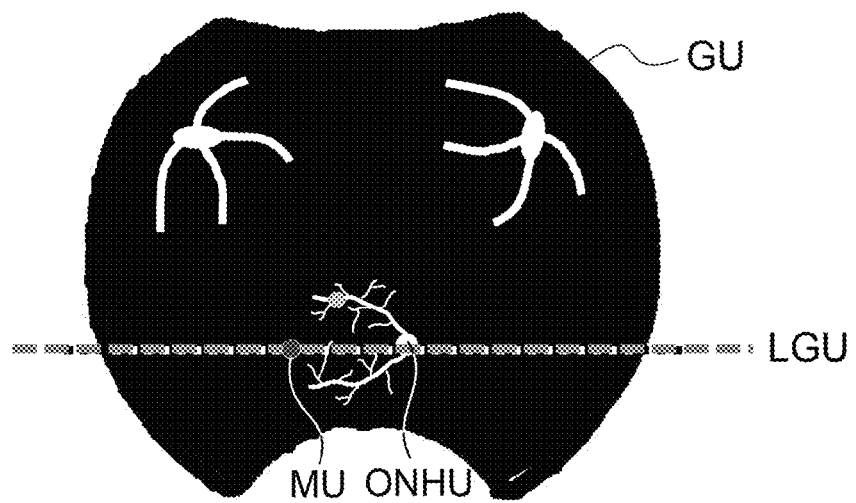
FIG. 12A is a diagram illustrating a line segment LGU set in the UWF upward-looking fundus image GU.
Figure 12B:
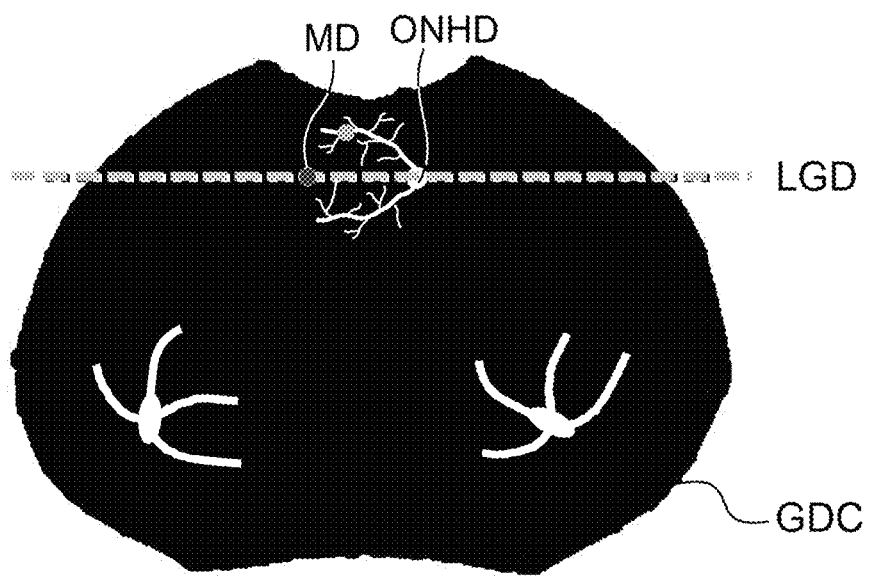
FIG. 12B is a diagram illustrating a line segment LGD set in the UWF downward-looking fundus image GD.

At step 346, the generated projection transformation grid is employed to transform the UWF downward-looking fundus image GD (see FIG. 7B) in order to obtain a post-transformation UWF downward-looking fundus image GDC (see FIG. 12B). After performing transformation using the projection transformation grid, the feature point group 1 and the feature point group 2 are brought to matching positions to complete the positional alignment processing. As a result of this transformation, the UWF downward-looking fundus image GDC is larger (has a greater area) than the UWF downward-looking fundus image GD.

In the foregoing explanation, the projection transformation grid is generated in order to map the UWF downward-looking fundus image GD onto the UWF upward-looking fundus image GU, and the UWF downward-looking fundus image GD is then transformed. Conversely, a projection transformation grid may be generated in order to map the UWF upward-looking fundus image GU onto the UWF downward-looking fundus image GD, before transforming the UWF upward-looking fundus image GU.

This completes the processing to align positions between the images, namely step 324 in FIG. 10, after which the montage image creation processing proceeds to step 326.

At step 326 in FIG. 10, the combined image generation section 1424 combines the UWF upward-looking fundus image GU with the post-transformation UWF downward-looking fundus image GDC in order to generate a montage image GM.

First, as illustrated in FIG. 12A, a line segment LGU is set in the UWF upward-looking fundus image GU so as to pass through the optical nerve head ONHU and the macula MU. Similarly, as illustrated in FIG. 12B, a line segment LGD is set in the post-transformation UWF downward-looking fundus image GDC so as to pass through the optical nerve head ONHD and the macula MD.

Next, the combined image generation section 1424 performs weighting processing for a region where the UWF upward-looking fundus image GU and the UWF downward-looking fundus image GDC overlap. As illustrated in FIG. 13, the combined image generation section 1424 applies a weighting of "1" to an upper UWF upward-looking fundus image GUx region that is a region on the upper side of the line segment LGU in the UWF upward-looking fundus image GU. The combined image generation section 1424 applies a weighting of "0" to a region on the upper side of the line segment LGU. The combined image generation section 1424 also applies a weighting of "1" to a lower UWF downward-looking fundus image GDCx region on the lower side of the line segment LGD in the post-transformation UWF downward-looking fundus image, and applies a weighting of "0" to a region on the upper side of the line segment LGD.

The combined image generation section 1424 performs weighting processing on the UWF upward-looking fundus image GU and the UWF downward-looking fundus image GDC in this manner in order to generate the montage image GM in which the UWF upward-looking fundus image GUx and the UWF downward-looking fundus image GDCx are combined. As illustrated in FIG. 13, a line segment LG is a line segment joining the optical nerve head ONHD and the macula M, the UWF upward-looking fundus image GUx is at the upper side of the line segment LG, and the UWF downward-looking fundus image GDCx is at the lower side of the line segment LG. The montage image is an example of a "combined image" of technology disclosed herein.

Note that the weighting relating to overlapping portions of the UWF upward-looking fundus image GU and the UWF downward-looking fundus image GDC is not limited to the above example, and various values may be employed in the mixing ratio between the UWF upward-looking fundus image GU and the UWF downward-looking fundus image GDC.

The UWF upward-looking fundus image GU and the UWF downward-looking fundus image GDC are positionally aligned and combined in the above manner. Combining in this manner enables a fundus image to be obtained for analyzing vortex veins and choroid blood vessels peripheral to the vortex veins, or for analyzing abnormalities or pathological lesions at positions in the fundus-peripheral portion or a fundus equatorial portion, without blood vessels of the fundus appearing discontinuous.

At the next step 328, the vortex vein analysis section 1425 uses the montage image GM to analyze the positions of vortex veins and blood vessel diameters of blood vessels in the vicinity of the vortex veins. Vortex vein information obtained as a result of this analysis includes information relating to the number of vortex veins, the positions of the vortex veins, the number of blood vessels connected to the vortex veins, and the blood vessel diameters of blood vessels surrounding the vortex-veins film.

At step 330, the display control section 1430 generates a display screen 400, described later, reflecting both the montage image and the patient attribute information (patient name, age, information indicating whether each fundus image corresponds to a left eye or a right eye, visual acuity, imaging date and time, and the like) corresponding to the patient ID.

At step 332, the output section 1440 outputs the montage image GM and vortex vein analysis information obtained by the vortex vein analysis to the storage device 254 of the server 140. The montage image GM and the vortex vein analysis information obtained by the vortex vein analysis are then stored in the storage device 254 of the server 140.

Also at step S332, the output section 1440 outputs image data corresponding to the display screen 400 to the viewer 150.

Note that the display control section 1430 may perform output so as to display the montage image GM on the display 256.

Explanation has been given according to the flowcharts of FIG. 10 and FIG. 11, in which the UWF downward-looking fundus image is transformed with reference to the UWF upward-looking fundus image. However, there is no limitation thereto, and the UWF upward-looking fundus image may be transformed with reference to the UWF downward-looking fundus image.

Although the montage image is generated employing binarized images, a similar technique may be applied to generate a montage image employing the color UWF upward-looking fundus image RG and UWF downward-looking fundus image RG that have not yet been subjected to binarization. In such cases, binarization processing may be performed on the montage image after performing montage combining processing.

Explanation follows regarding a graphical user interface (GUI) in which the montage image is employed.

As described above, at step 332 in FIG. 10, the server 140 outputs image data compatible with the display screen 400 to the viewer 150.

Having received the image data output from the server 140, the viewer 150 displays the display screen 400 on a non-illustrated display (monitor).

Figure 14:
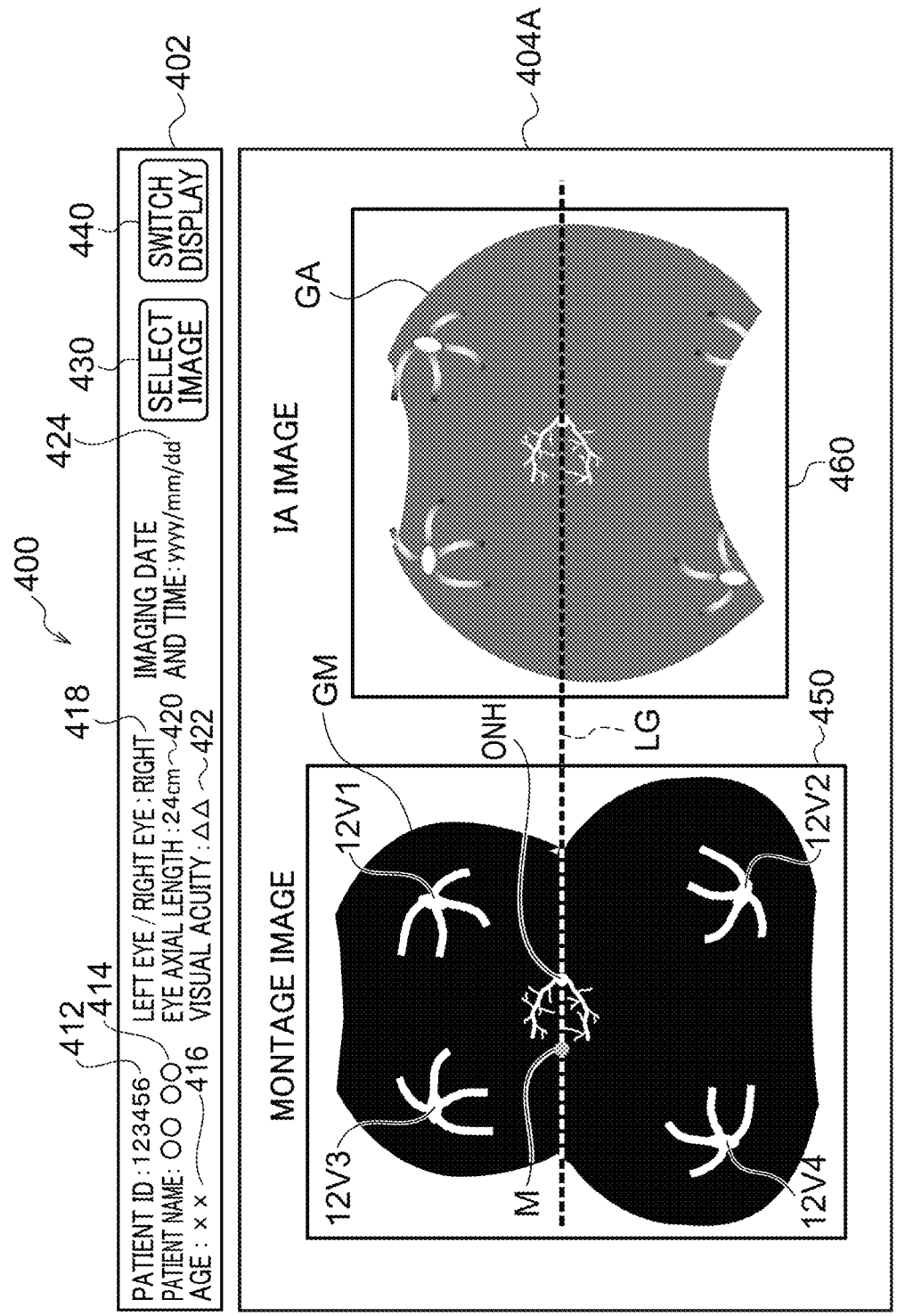
FIG. 14 is a diagram illustrating a first display mode of a display screen 400 of a display 256 of a viewer 150.

As illustrated in FIG. 14, the display screen 400 includes an information display region 402 and an image display region 404 (404A). Note that FIG. 14 illustrates an image display region 404A corresponding to a first display mode of the image display region 404. The information display region 402 includes a patient ID display region 412, a patient name display region 414, an age display region 416, a left eye/right eye display region 418, an eye axial length display region 420, a visual acuity display region 422, and an imaging date and time display region 424. The viewer 150 displays various information in the respective display regions from the patient ID display region 412 to the imaging date and time display region 424 based on the received information.

The information display region 402 is also provided with a select image icon 430 and a switch display icon 440.

The image display region 404A includes a montage image display region 450 and a related image display region 460. When the select image icon 430 has been selected, a pull-down menu is displayed. The pull-down menu displayed when the select image icon 430 has been selected is a menu for selecting a related image for display in the related image display region 460. For example, the pull-down menu displays selection candidates including an animation of previously-acquired fluorescence images of the fundus of the examined eye 12 (for example indocyanine green angiography images (IA images)), a still IA image, and a UWF en face fundus image. FIG. 14 illustrates a case in which the montage image GM is being displayed in the montage image display region 450 and an animation GA of IA images is being displayed in the related image display region 460.

The line segment LG is a line segment joining the optical nerve head ONH and the macula M in the montage image GM. The animation GA of IA images displayed in the related image display region 460 is displayed such that the positions of the optical nerve head and the macula in the animation GA are aligned so as to lie on the line segment LG.

The user is able to select whether the line segment LG is displayed or hidden.

Marks to indicate vortex veins may be displayed in the montage image and the related image at positions corresponding to the vortex veins.

For example, as illustrated in FIG. 14, in the montage image GM the positions of the vortex veins 12V1, 12V2, 12V3, 12V4 may be detected and marks to indicate the vortex veins may be displayed at the detected positions in the montage image GM.

Moreover, the vortex vein analysis information (the number of vortex veins, the positions of the vortex veins, the number of blood vessels connected to the vortex veins, and the blood vessel diameters of blood vessels surrounding the vortex veins) may also be displayed on the display screen 400.

When the switch display icon 440 has been selected, a pull-down menu is displayed. The pull-down menu includes menu options relating to image display in the image display region 404. Specifically, the pull-down menu includes a menu option to display the montage image and the IA image alongside each other, menu options to divide and combine display of the montage image and the IA image respectively, and a menu option to display the montage image alongside a 3D image obtained using a 3D model, namely by projecting the montage image onto the 3D model. FIG. 14 illustrates a case in which the menu option to display the montage image and the IA image alongside each other has been selected.

On the other hand, FIG. 15 illustrates a case in which the menu option to divide and combine display of the montage image and the IA image has been selected from the pull-down menu of the switch display icon 440. As illustrated in FIG. 15, a dividing line LK is employed as a boundary, with an IA image (animation or still image) GA being displayed at the upper side of the dividing line LK, and a montage image GM being displayed at the lower side of the dividing line LK in an image display region 404B. By moving the dividing line LK up or down using an icon I, the dividing line LK changes the regions in which the IA image GA and the montage image GM are displayed. For example, when the icon I is moved toward the upper side, the dividing line LK is moved toward the upper side, and only portions of the IA image GA lying at the upper side of the dividing line LK after moving toward the upper side are displayed, whereas portions of the montage image GM lying between the former position of the dividing line LK and the new position of the dividing line LK are displayed.

FIG. 16 illustrates a case in which the menu option to display the montage image alongside a 3D image has been selected from the pull-down menu of the switch display icon 440. As illustrated in FIG. 16, an image display region 404C includes the montage image display region 450 and a 3D image display region 470 displaying a 3D image obtained by projecting the montage image onto a 3D model of an eyeball. Note that the 3D model of an eyeball may first be corrected based on the eye axial length data of the patient as received from the server 140 in order to project the montage image onto a 3D model corresponding to the examined eye.

Note that a menu option to display all may be added to the pull-down menu of the switch display icon 440, such that two or more of the image display region 404A to the image display region 404C illustrated in FIG. 14 to FIG. 16 are displayed simultaneously or sequentially on a single screen.

Instead of employing the montage image GM after binarization, configuration may be made to display a montage image obtained by combining the UWF upward-looking fundus image and the UWF downward-looking fundus image prior to binarization on the 3D model.

As described above, in the present exemplary embodiment, the montage image is generated by combining the UWF upward-looking fundus images and the UWF downward-looking fundus images, thereby enabling an ophthalmologist to diagnose the examined eye of the patient more accurately using the montage image, in which regions corresponding to both the fundus equatorial portion and the fundus-peripheral portion are captured. In particular, the montage image can be generated without the eyelid, eyelashes, or equipment appearing in the image. This enables the ophthalmologist to ascertain the state of both upper and lower vortex veins. Moreover, it is possible to diagnose whether or not pathological lesions are present in the fundus equatorial portion and the fundus-peripheral portion. Moreover, it is possible to deduce not only pathological lesions in the fundus equatorial portion and the fundus-peripheral portion, but also advance indicators of pathological lesions in the fundus central portion from the states of the upper and lower vortex veins.

Next, explanation follows regarding various modified examples.

FIRST MODIFIED EXAMPLE

In the exemplary embodiment described above, montage image creation processing is executed by the CPU 262 of the server 140. However, technology disclosed herein is not limited thereto. For example, montage image creation processing may be executed by the CPU 22 of the ophthalmic device 110, executed by a CPU of the viewer 150, or executed by a CPU of another computer connected over the network 130.

SECOND MODIFIED EXAMPLE

In the exemplary embodiment described above, the UWF upward-looking fundus images and the UWF downward-looking fundus images are acquired in the following manner. Namely, the upper fixation light 92U is illuminated and the UWF upward-looking fundus image GU of the examined eye 12 is acquired in a state in which the gaze of the patient is directed upward. The lower fixation light 92D is then illuminated and the UWF downward-looking fundus image GD of the examined eye 12 is acquired in a state in which the gaze of the patient is directed downward. However, technology disclosed herein is not limited thereto. For example, the SLO unit 40 may be configured so as to be capable of swinging in an up-down direction centered on the center of the pupil of the examined eye 12.

When acquiring an upward image, the SLO unit 40 is swung toward the lower side centered on the center of the pupil of the examined eye 12. In this state, the SLO unit 40 on the lower side acquires an image of the fundus through the pupil of the examined eye 12 on the upper side. When this is performed, the upper fixation light 92U may also be illuminated to direct the gaze of the patient upward.

When acquiring a downward image, the SLO unit 40 is swung toward the upper side centered on the center of the pupil of the examined eye 12. In this state, the SLO unit 40 on the upper side acquires an image of the fundus through the pupil of the examined eye 12 on the lower side. When this is performed, the lower fixation light 92D may also be illuminated to direct the gaze of the patient downward.

Moreover, there is no limitation to directing the gaze of the patient in the up-down direction or swinging the SLO unit 40 in the up-down direction centered on the center of the pupil of the examined eye 12.

For example, fixation lights may be provided to guide the gaze of the examined eye 12 toward an oblique upper right side, an oblique upper left side, an oblique lower right side, and an oblique lower left side, and fundus images may be acquired with the gaze in respective corresponding states and then combined to generate a montage image.

Furthermore, the SLO unit 40 may be configured capable of swinging toward an oblique upper right side, an oblique upper left side, an oblique lower right side, and an oblique lower left side centered on the center of the pupil of the examined eye 12 to enable imaging of the fundus through the pupil of the examined eye 12. The SLO unit 40 may acquire UWF fundus images corresponding to each direction by imaging the fundus from each direction, which are then combined to generate a montage image. In such cases, respective fixation lights disposed on the oblique upper right side, the oblique upper left side, the oblique lower right side, and the oblique lower left side may be illuminated to guide the gaze of the examined eye 12 in each of the directions.

THIRD MODIFIED EXAMPLE

As well as visualizing vortex veins, the montage image generated by the server 140 may by subjected to processing to analyze retinal structures or analyze blood vessels or to detect abnormal regions (pathological lesions) in the fundus-peripheral portion (fundus equatorial portion). The generated montage image may be employed to deduce the presence of pathological lesions (or the possibility of pathological lesions developing) in the fundus central portion, for example diabetic retinopathy, age-related macular degeneration, and the like. Factoring in image information from the fundus-peripheral portion (fundus equatorial portion) in the montage image enables image analysis of the fundus central portion image to be used to deduce pathological lesions in consideration of information relating to the fundus-peripheral portion.

Moreover, artificial intelligence (AI) based analysis may be employed for structural analysis and blood vessel analysis, or as analysis to deduce pathological lesions.

Processing to perform structural analysis of the retina, to analyze blood vessels, or to detect abnormal regions (pathological lesions) in the fundus-peripheral portion (fundus equatorial portion) may be carried out using the functionality of the vortex vein analysis section 1425, or may be implemented by another, non-illustrated, image analysis section.

FOURTH MODIFIED EXAMPLE

In the exemplary embodiment described above, the CPU 262 of the server 140 executes the montage image creation processing, and the positional alignment processing is performed automatically. In cases in which the montage image creation processing is performed by the viewer 150, extraction of the feature point group 1 from the UWF upward-looking fundus images and extraction of the feature point group 2 from the UWF downward-looking fundus images may be performed manually by a user.

Specifically, the following processing may be executed in place of steps 340, 342 in FIG. 11.

Image data of the UWF upward-looking fundus image GU and the UWF downward-looking fundus image GD are transmitted from the server 140 to the viewer 150.

Having received the image data, the viewer 150 detects the macula MU, MD and the optical nerve head ONHU, ONHD in the UWF upward-looking fundus image GU and the UWF downward-looking fundus image GD respectively. As illustrated in FIG. 17, the viewer 150 displays the UWF upward-looking fundus image GU and the UWF downward-looking fundus image GD alongside each other, positionally aligned such that a line segment joining the macula MU and the optical nerve head ONHU in the UWF upward-looking fundus image GU and a line segment joining the macula MID and the optical nerve head ONHD in the UWF downward-looking fundus image GD line up with each other to configure a line segment LGM. The viewer 150 then sets a feature point extraction region upper limit LU and a feature point extraction region lower limit LD running parallel to the line segment LGM at positions at predetermined distances to the upper side and the lower side of the line segment LGM.

The user then sets the feature point group 1 between the upper limit LU and the lower limit LD in the UWF upward-looking fundus image GU. The user then extracts the feature point group 2 corresponding to the feature point group 1 between the upper limit LU and the lower limit LD in the UWF downward-looking fundus image GD. The viewer 150 then transmits data indicating the positions of the feature point group 1 and the feature point group 2 to the server 140. Having received the data indicating the positions of the feature point group 1 and the feature point group 2, at step 344 (FIG. 11) the position alignment section 1421 of the server 140 creates the projection transformation grid described above using the received feature point group 1 and feature point group 2 (see FIG. 11).

OTHER MODIFIED EXAMPLES

The montage image creation processing and the processing when displaying the montage image described above are merely examples. Obviously, unnecessary steps may be removed, additional steps may be introduced, and the processing sequence may be changed within a range not departing from the spirit thereof.

The ophthalmic device 110 has functionality to image a region with an internal irradiation angle of 200° relative to the position of the eyeball center 170 of the examined eye 12 (an external irradiation angle of 167° relative to the pupil of the eyeball of the examined eye 12). However, the angle of view is not limited thereto. The internal irradiation angle may be set to 200° or greater (and the external irradiation angle may be set to from 167° to) 180°.

Moreover, specifications may be adjusted such that the internal irradiation angle is set to less than 200° (the external irradiation angle is set to less than 167°). For example, an angle of view with an internal irradiation angle of approximately 180° (an external irradiation angle of approximately 140°), an internal irradiation angle of approximately 156° (an external irradiation angle of approximately 120°), or an internal irradiation angle of approximately 144° (an external irradiation angle of approximately 110°) may be adopted. These values are merely examples, and any angle of view enabling the fundus-peripheral portion and the fundus central portion in which vortex veins and the like are present to be captured in a single take may be adopted.

In the respective examples described above, processing is implemented by a software configuration using a computer. However, technology disclosed herein is not limited thereto. For example, processing may be implemented solely by a hardware configuration such as a field-programmable gate array (FPGA) or an application specific integrated circuit (ASIC) instead of by a software configuration using a computer. Alternatively, some of the tomographic image generation processing may be implemented by a software configuration, with the remaining processing being implemented by a hardware configuration.

The invention claimed is:

1. An image processing method comprising:
    acquiring a first direction fundus image imaged in a state in which a gaze of an examined eye is directed in a first direction, and a second direction fundus image imaged in a state in which the examined eye is directed in a second direction different from the first direction;
    generating a transformed image by transforming one fundus image of the first direction fundus image and the second direction fundus image;
    generating a combined image by combining the transformed image and the other fundus image of the first direction fundus image and the second direction fundus image; and
    outputting the combined image,
    wherein generating the transformed image comprises:
    respectively extracting at least four feature points on the fundus of the examined eye, from the first direction fundus image and the second direction fundus image; and
    generating the transformed image, in which the at least four feature points of the other fundus image are matched to the at least four feature points of the one fundus image, by projectively transforming the one fundus image, and
    wherein generating the combined image comprises:
        performing a first weighting processing in the transformed image, with respect to a first region where the transformed image and the other fundus image overlap;

performing a second weighting processing in the other fundus image, with respect to a second region where the transformed image and the other fundus image overlap; and combining the transformed image and the other fundus image based on performing the first weighting processing and performing the second weighting processing.

2. The image processing method of claim 1, wherein:
the first direction is a direction when the examined eye is caused to look upward; and
the second direction is a direction when which the examined eye is caused to look downward.

3. The image processing method of claim 1, wherein the first direction fundus image and the second direction fundus image are imaged using an imaging device having an angle of view that enables a range spanning at least from a fundus posterior pole to a fundus-peripheral portion to be imaged in a single take.

4. The image processing method of claim 1, wherein a fundus equatorial portion is included in a fundus-peripheral portion.

5. The image processing method of claim 1, wherein the first direction fundus image and the second direction fundus image are imaged using an imaging device having an angle of view of at least 200° as referenced against an eyeball center of the examined eye.

6. The image processing method of claim 1, wherein:
the first direction fundus image is obtained by imaging a fundus upper side of a fundus-peripheral region including at least an optical nerve head and an upper side vortex vein; and
the second direction fundus image is obtained by imaging a lower side of a fundus-peripheral region including at least the optical nerve head and a lower side vortex vein.

7. The image processing method of claim 1, further comprising employing the combined image to perform fundus-peripheral portion analysis processing.

8. The image processing method of claim 1, further comprising employing the combined image to perform vortex vein analysis processing.

9. A non-transitory storage medium storing instructions that, when executed by a computer, cause the computer to perform a method comprising:
acquiring a first direction fundus image imaged in a state in which an examined eye is directed in a first direction, and a second direction fundus image imaged in a state in which the examined eye is directed in a second direction different from the first direction;
generating a transformed image by transforming one fundus image of the first direction fundus image and the second direction fundus image;
generating a combined image by combining the transformed image and the other fundus image of the first direction fundus image and the second direction fundus image; and
outputting the combined image,
wherein generating the transformed image comprises:
respectively extracting at least four feature points on the fundus of the examined eye, from the first direction fundus image and the second direction fundus image; and
generating the transformed image, in which the at least four feature points of the other fundus image are matched to the at least four feature points of the one fundus image, by projectively transforming the one fundus image, and
wherein generating the combined image comprises:
performing a first weighting processing in the transformed image, with respect to a first region where the transformed image and the other fundus image overlap;
performing a second weighting processing in the other fundus image, with respect to a second region where the transformed image and the other fundus image overlap; and
combining the transformed image and the other fundus image based on performing the first weighting processing and performing the second weighting processing.

* * * * *